US011229909B2

(12) United States Patent
Agah et al.

(10) Patent No.: US 11,229,909 B2
(45) Date of Patent: Jan. 25, 2022

(54) FLOW CELL WITH SELECTIVE DEPOSITION OR ACTIVATION OF NUCLEOTIDES

(71) Applicant: ILLUMINA, INC., San Diego, CA (US)

(72) Inventors: Ali Agah, Menlo Park, CA (US); Aathavan Karunakaran, Berkeley, CA (US); Tarun Khurana, Freemont, CA (US); Stanley Hong, Palo Alto, CA (US); Merek Siu, Alameda, CA (US); Arvin Emadi, San Jose, CA (US); Craig Ciesla, Mountain View, CA (US)

(73) Assignee: ILLUMINA, INC., San Diego, CA (US)

( * ) Notice: Subject to any disclaimer, the term of this patent is extended or adjusted under 35 U.S.C. 154(b) by 0 days.

(21) Appl. No.: 17/254,469

(22) PCT Filed: May 26, 2020

(86) PCT No.: PCT/US2020/034510
§ 371 (c)(1),
(2) Date: Dec. 21, 2020

(87) PCT Pub. No.: WO2020/243072
PCT Pub. Date: Dec. 3, 2020

(65) Prior Publication Data
US 2021/0146356 A1    May 20, 2021

Related U.S. Application Data

(60) Provisional application No. 62/855,657, filed on May 31, 2019.

(51) Int. Cl.
*G01N 35/00* (2006.01)
*G01N 33/00* (2006.01)
(Continued)

(52) U.S. Cl.
CPC ..... *B01L 3/502715* (2013.01); *B01J 19/0046* (2013.01); *B01L 3/502707* (2013.01);
(Continued)

(58) Field of Classification Search
CPC ............ B01J 19/0046; B01J 2300/0645; B01J 2300/0816; C12Q 1/6874; C12N 15/09; G01N 35/00; G01N 33/00; A61J 1/06
See application file for complete search history.

(56) References Cited

U.S. PATENT DOCUMENTS 7,414,116 B2    8/2008  Milton et al.
8,906,320 B1   12/2014  Eltoukhy et al.
(Continued)

FOREIGN PATENT DOCUMENTS

WO    WO 1998/001221 A1   1/1998
WO    WO 2009/031105 A2   3/2009

OTHER PUBLICATIONS

International Search Report and Written Opinion dated Aug. 25, 2020 for International Application No. PCT/US2020/034510, 10 pages.

*Primary Examiner* — Brian J. Sines
(74) *Attorney, Agent, or Firm* — Frost Brown Todd LLC

(57) ABSTRACT

An apparatus includes a flow cell body, a plurality of electrodes, an integrated circuit, and an imaging assembly. The flow cell body defines one or more flow channels and a plurality of wells. Each flow channel is configured to receive a flow of fluid. Each well is fluidically coupled with the corresponding flow channel. Each well is configured to contain at least one polynucleotide. Each electrode is positioned in a corresponding well of the plurality of wells. The electrodes are operable to effect writing of polynucleotides in the corresponding wells. The integrated circuit is operable to drive selective deposition or activation of selected nucleotides to attach to polynucleotides in the wells to thereby
(Continued)

generate polynucleotides representing machine-written data in the wells. The imaging assembly is operable to capture images indicative of one or more nucleotides in a polynucleotide.

6 Claims, 8 Drawing Sheets

(51) Int. Cl.
*A61J 1/06* (2006.01)
*C12N 15/09* (2006.01)
*C12Q 1/6874* (2018.01)
*B01L 3/00* (2006.01)
*G11C 13/02* (2006.01)
*B01J 19/00* (2006.01)

(52) U.S. Cl.
CPC ........ *B01L 3/502738* (2013.01); *G11C 13/02* (2013.01); *B01J 2219/00711* (2013.01); *B01J 2219/00713* (2013.01); *B01J 2219/00722* (2013.01); *B01L 2200/026* (2013.01); *B01L 2300/0645* (2013.01); *B01L 2300/0816* (2013.01); *B01L 2300/0867* (2013.01); *B01L 2400/0487* (2013.01); *B01L 2400/0622* (2013.01); *B01L 2400/0655* (2013.01); *B01L 2400/08* (2013.01); *C12N 15/09* (2013.01); *C12Q 1/6874* (2013.01)

(56) References Cited

U.S. PATENT DOCUMENTS

| | | | |
|---|---|---|---|
| 9,012,022 B2 | 4/2015 | George et al. | |
| 9,453,258 B2 | 9/2016 | Kain et al. | |
| 9,512,422 B2 | 12/2016 | Barnard et al. | |
| 10,254,225 B2 | 4/2019 | Zhong et al. | |
| 2015/0261664 A1 | 9/2015 | Goldman et al. | |
| 2016/0002718 A1 | 1/2016 | Buermann et al. | |
| 2016/0089651 A1* | 3/2016 | Banyai | B01J 19/0046 506/40 |
| 2018/0101487 A1 | 4/2018 | Peck | |
| 2018/0117587 A1 | 5/2018 | Lemoine et al. | |
| 2018/0137418 A1* | 5/2018 | Roquet | C12N 9/22 |
| 2019/0118154 A1* | 4/2019 | Marsh | B01J 19/0046 |
| 2019/0244109 A1* | 8/2019 | Bramlett | G06N 3/123 |
| 2019/0318132 A1* | 10/2019 | Peck | C12N 15/1089 |

\* cited by examiner

FLOW CELL WITH SELECTIVE DEPOSITION OR ACTIVATION OF NUCLEOTIDES

RELATED APPLICATION

This application is a national stage entry of International Patent Application No. PCT/US2020/034510, entitled "Flow Cell with Selective Deposition or Activation of Nucleotides," filed on May 26, 2020, which claims priority to U.S. Provisional Patent App. No. 62/855,657, entitled "Flow Cell with Selective Deposition or Activation of Nucleotides," filed on May 31, 2019, which is incorporated by reference herein in its entirety.

BACKGROUND

Computer systems have used various different mechanisms to store data, including magnetic storage, optical storage, and solid-state storage. Such forms of data storage may present drawbacks in the form of read-write speed, duration of data retention, power usage, or data density.

Just as naturally occurring DNA may be read, machine-written DNA may also be read. Pre-existing DNA reading techniques may include an array-based, cyclic sequencing assay (e.g., sequencing-by-synthesis (SBS)), where a dense array of DNA features (e.g., template nucleic acids) are sequenced through iterative cycles of enzymatic manipulation. After each cycle, an image may be captured and subsequently analyzed with other images to determine a sequence of the machine-written DNA features. In another biochemical assay, an unknown analyte having an identifiable label (e.g., fluorescent label) may be exposed to an array of known probes that have predetermined addresses within the array. Observing chemical reactions that occur between the probes and the unknown analyte may help identify or reveal properties of the analyte.

SUMMARY

Described herein are devices, systems, and methods for selectively activating or depositing nucleotides within a flow cell.

An implementation relates to an apparatus comprising a flow cell body defining one or more flow channels and a plurality of wells, each flow channel of the one or more flow channels to receive a flow of fluid. In some such implementations, each well of the plurality of wells may be fluidically coupled with the corresponding flow channel of the one or more flow channels, each well of the plurality of wells to contain at least one polynucleotide. In some such implementations, the apparatus may comprise a plurality of electrodes. In some such implementations, each electrode of the plurality of electrodes may be positioned in a corresponding well of the plurality of wells, the plurality of electrodes to effect writing of polynucleotides in the corresponding wells of the plurality of wells. In some such implementations, the apparatus may comprise an integrated circuit, the integrated circuit to drive selective deposition or activation of selected nucleotides to attach to polynucleotides in the wells of the plurality of wells to thereby generate polynucleotides representing machine-written data in the plurality of wells. In some such implementations, the apparatus may comprise an imaging assembly to capture images indicative of one or more nucleotides in a polynucleotide.

Variations on any one or more of the above implementations exist, wherein each electrode of the plurality of electrodes may define an aperture.

Variations on any one or more of the above implementations exist, wherein the imaging assembly may include at least one image sensor to receive light through the aperture of each electrode of the plurality of electrodes.

Variations on any one or more of the above implementations exist, wherein each electrode of the plurality of electrodes may be annularly shaped.

Variations on any one or more of the above implementations exist, wherein the plurality of electrodes may comprise a plurality of electrode segments arranged in quadrants, the aperture being defined at a central region of the arrangement of quadrants.

Variations on any one or more of the above implementations exist, wherein the integrated circuit may be further in communication with the imaging assembly.

Variations on any one or more of the above implementations exist, wherein the integrated circuit may comprise a CMOS chip.

Variations on any one or more of the above implementations exist, wherein the plurality of wells may be formed as a plurality of discrete recesses arranged in a pattern along a floor of the corresponding flow channel of the one or more flow channels.

Variations on any one or more of the above implementations exist, wherein each well of the plurality of wells may be defined by at least one sidewall and a floor.

Variations on any one or more of the above implementations exist, wherein each electrode of the plurality of electrodes may be positioned on the floor of the corresponding well of the plurality of wells.

Variations on any one or more of the above implementations exist, wherein each electrode of the plurality of electrodes may be positioned on a sidewall of the at least one sidewall of the corresponding well.

Variations on any one or more of the above implementations exist, wherein the floor of each well of the plurality of wells may further define an aperture, the aperture to provide a path for fluid communication between the well of the plurality of wells and a fluid source.

Variations on any one or more of the above implementations exist, wherein the integrated circuit to drive the plurality of electrodes to selectively deposit or activate selected nucleotides by applying a voltage within the corresponding well of the plurality of wells.

Variations on any one or more of the above implementations exist, wherein each nucleotide may be associated with a particular voltage, the integrated circuit to drive the electrodes of the plurality of electrodes to selectively deposit or activate a selected nucleotide by applying the particular voltage associated with the selected nucleotide.

Variations on any one or more of the above implementations exist, wherein each well of the plurality of wells may include a set of four electrodes from the plurality of electrodes, each electrode in the set of four being associated with a corresponding voltage of the particular voltages associated with the nucleotides, such that each electrode in the set of four corresponds with a particular one of four nucleotides.

Variations on any one or more of the above implementations exist, wherein the integrated circuit to drive the selective deposition or activation of selected nucleotides by applying a change in pH within the corresponding well of the plurality of wells.

Variations on any one or more of the above implementations exist, wherein the apparatus may further comprise at least one light source, the integrated circuit to drive the selective deposition or activation of selected nucleotides by activating the at least one light source.

Variations on any one or more of the above implementations exist, wherein each nucleotide may be associated with a particular wavelength of light, the integrated circuit to drive the at least one light source to selectively deposit or activate a selected nucleotide by applying the particular wavelength of light associated with the selected nucleotide.

Variations on any one or more of the above implementations exist, wherein the integrated circuit to drive the selective deposition or activation of selected nucleotides by applying a change in pH within the corresponding well of the plurality of wells in addition to driving the activation of the at least one light source.

Variations on any one or more of the above implementations exist, wherein the at least one light source may comprise a light matrix.

Variations on any one or more of the above implementations exist, wherein the light matrix may comprise a matrix of microscopic light emitting diodes.

Variations on any one or more of the above implementations exist, wherein the light matrix to project light onto a bottom of each well of the plurality of wells.

Variations on any one or more of the above implementations exist, wherein the light matrix may be positioned under a bottom of each well of the plurality of wells.

Variations on any one or more of the above implementations exist, wherein the apparatus may further comprise one or more polarizers, the integrated circuit to drive the selective deposition or activation of selected nucleotides by activating the at least one polarizer of the one or more polarizers in coordination with the at least one light source.

Variations on any one or more of the above implementations exist, wherein the integrated circuit to drive the selective deposition or activation of selected nucleotides by activating communication of pre-charged enzymes to the one or more flow channels.

Variations on any one or more of the above implementations exist, wherein the apparatus may further comprise a printhead, the integrated circuit to drive the selective deposition or activation of selected nucleotides by activating the printhead.

Variations on any one or more of the above implementations exist, wherein each nozzle of the four nozzles to dispense a corresponding nucleotide.

Variations on any one or more of the above implementations exist, wherein the integrated circuit further to drive acoustic tamping of droplets emitted by the printhead.

Variations on any one or more of the above implementations exist, wherein the integrated circuit further to activate the printhead and the plurality of electrodes in cooperation to thereby drive the selective deposition or activation of selected nucleotides.

Another implementation relates to an apparatus comprising a flow cell body defining one or more flow channels and a plurality of wells, each flow channel of the one or more flow channels to receive a flow of fluid. In some such implementations, each well of the plurality of wells may be fluidically coupled with the corresponding flow channel of the one or more flow channels, each well of the plurality of wells to contain at least one polynucleotide. In some such implementations, the apparatus may comprise a plurality of electrodes. In some such implementations, each electrode of the plurality of electrodes may be positioned in a corresponding well of the plurality of wells, the plurality of electrodes to effect writing of polynucleotides in the corresponding wells of the plurality of wells. In some such implementations, the apparatus may comprise an integrated circuit, the integrated circuit to drive selective deposition or activation of selected nucleotides to attach to polynucleotides in the plurality of wells to thereby generate polynucleotides representing machine-written data in the plurality of wells, each nucleotide being associated with a particular voltage, the integrated circuit to drive the plurality of electrodes to selectively deposit or activate a selected nucleotide by applying the particular voltage associated with the selected nucleotide.

Variations on any one or more of the above implementations exist, wherein each well of the plurality of wells may include a set of four electrodes from the plurality of electrodes, each electrode in the set of four being associated with a corresponding voltage of the particular voltages associated with the nucleotides, such that each electrode in the set of four corresponds with a particular one of four nucleotides.

Yet another implementation relates to an apparatus comprising a flow cell body defining one or more flow channels and a plurality of wells, each flow channel of the one or more flow channels to receive a flow of fluid. In some such implementations, each well of the plurality of wells may be fluidically coupled with the corresponding flow channel of the one or more flow channels, each well of the plurality of wells to contain at least one polynucleotide. In some such implementations, the apparatus may comprise a plurality of electrodes. In some such implementations, each electrode of the plurality of electrodes may be positioned in a corresponding well of the plurality of wells, the plurality of electrodes to effect writing of polynucleotides in the corresponding wells of the plurality of wells. In some such implementations, the apparatus may comprise at least one light source. In some such implementations, the apparatus may comprise an integrated circuit, the integrated circuit to drive selective deposition or activation of selected nucleotides to attach to polynucleotides in the plurality of wells to thereby generate polynucleotides representing machine-written data in the plurality of wells, the integrated circuit to drive the selective deposition or activation of selected nucleotides by activating the at least one light source.

Variations on any one or more of the above implementations exist, wherein each nucleotide may be associated with a particular wavelength of light, the integrated circuit to drive the at least one light source to selectively deposit or activate a selected nucleotide by applying the particular wavelength of light associated with the selected nucleotide.

Variations on any one or more of the above implementations exist, wherein the integrated circuit to drive the selective deposition or activation of selected nucleotides by applying a change in pH within the corresponding well of the plurality of wells in addition to driving the activation of the at least one light source.

Variations on any one or more of the above implementations exist, wherein the at least one light source may comprise a light matrix.

Variations on any one or more of the above implementations exist, wherein the light matrix may comprise a matrix of micro-LEDs.

Variations on any one or more of the above implementations exist, wherein the light matrix to project light onto a bottom of each well of the plurality of wells.

Variations on any one or more of the above implementations exist, wherein the light matrix may be positioned under a bottom of each well of the plurality of wells.

Variations on any one or more of the above implementations exist, wherein the apparatus may further comprise one or more polarizers, the integrated circuit to drive the selective deposition or activation of selected nucleotides by activating the one or more polarizers in coordination with the at least one light source.

Yet another implementation relates to an apparatus comprising a flow cell body defining one or more flow channels and a plurality of wells, each flow channel of the one or more flow channels to receive a flow of fluid. In some such implementations, each well of the plurality of wells may be fluidically coupled with the corresponding flow channel of the one or more flow channels, each well of the plurality of wells to contain at least one polynucleotide. In some such implementations, the apparatus may comprise a plurality of electrodes. In some such implementations, each electrode of the plurality of electrodes may be positioned in a corresponding well of the plurality of wells, the plurality of electrodes to effect writing of polynucleotides in the corresponding wells of the plurality of wells. In some such implementations, the apparatus may comprise a printhead to deposit nucleotides. In some such implementations, the apparatus may comprise an integrated circuit, the integrated circuit to drive selective deposition of selected nucleotides to attach to polynucleotides in the plurality of wells to thereby generate polynucleotides representing machine-written data in the plurality of wells, the integrated circuit to drive the selective deposition of selected nucleotides by activating the printhead.

Variations on any one or more of the above implementations exist, wherein the printhead may include four nozzles, each nozzle to dispense a corresponding nucleotide.

Variations on any one or more of the above implementations exist, wherein the integrated circuit further to drive acoustic tamping of droplets emitted by the printhead.

Variations on any one or more of the above implementations exist, wherein the integrated circuit further to activate the printhead and the plurality of electrodes in cooperation to thereby drive the selective deposition or activation of selected nucleotides.

Yet another implementation relates to a method comprising flowing a fluid through a flow channel of a flow cell. In some such implementations, the fluid may comprise a plurality of types of nucleotides, the flow cell may include a plurality of primary bases to support polynucleotides, the primary bases being secured to a floor region of the flow cell. In some such implementations, the method may comprise selecting one type of nucleotide for attachment to a selected primary base of the plurality of primary bases in the flow cell. In some such implementations, the method may comprise activating the selected one type of nucleotide to thereby cause the selected one type of nucleotide to attach to the selected primary base, the attached nucleotide representing machine-written data.

Variations on any one or more of the above implementations exist, wherein the method may further comprise repeating selecting one type of nucleotide for attachment to a selected primary base in the flow cell and activating the selected one type of nucleotide to thereby cause the selected one type of nucleotide to attach to the selected primary base, to thereby generate a polynucleotide on the primary base, the generated polynucleotide including a plurality of selected types of nucleotides, the generated polynucleotide representing machine-written data.

Variations on any one or more of the above implementations exist, wherein activating the selected type of nucleotide may comprise activating an electrode in the flow cell to thereby apply a voltage to the selected type of nucleotide.

Variations on any one or more of the above implementations exist, wherein, each type of nucleotide may be associated with a particular voltage, and activating the electrode may comprise activating the electrode to apply the particular voltage associated with the selected type of nucleotide.

I Variations on any one or more of the above implementations exist, wherein the flow cell may include electrodes associated with different corresponding voltages, and the method may further comprise selecting an electrode from the electrodes, the selected electrode corresponding to the voltage associated with the selected type of nucleotide, the activated electrode being the selected electrode.

Variations on any one or more of the above implementations exist, wherein activating the selected type of nucleotide may comprise applying a change in pH within the flow cell, the applied pH being associated with the selected type of nucleotide.

Variations on any one or more of the above implementations exist, wherein activating the selected type of nucleotide may comprise activating at least one light source.

Variations on any one or more of the above implementations exist, wherein each type of nucleotide may be associated with a particular wavelength of light, and activating at least one light source may comprise activating the at least one light source to emit light at the particular wavelength associated with the selected type of nucleotide.

Variations on any one or more of the above implementations exist, wherein activating the selected type of nucleotide may further comprise applying a change in pH within the flow cell in coordination with activating the at least one light source, the applied pH being associated with the selected type of nucleotide.

Variations on any one or more of the above implementations exist, wherein activating the selected type of nucleotide may further comprise activating at least one polarizer in coordination with activating the at least one light source.

Variations on any one or more of the above implementations exist, wherein activating the selected type of nucleotide may comprise communicating pre-charged enzymes to the flow channel.

Yet another implementation relates to a method comprising selecting one type of nucleotide for attachment to a selected primary base in a flow cell. In some such implementations, the method may comprise depositing the selected one type of nucleotide into the flow cell, the flow cell including a plurality of primary bases to support polynucleotides, the primary bases being secured to a floor region of the flow cell, the deposited nucleotide attaching to a corresponding primary base of the plurality of primary bases, the attached nucleotide representing machine-written data.

Variations on any one or more of the above implementations exist, wherein, depositing the selected type of nucleotide may comprise emitting the selected type of nucleotide from a printhead.

Variations on any one or more of the above implementations exist, wherein the printhead may include a plurality of nozzles, each nozzle of the plurality of nozzles being associated with a particular type of nucleotide. In some such implementations, the method may further comprise selecting the nozzle of the plurality of nozzles corresponding to the selected type of nucleotide, the deposited nucleotide being deposited from the selected nozzle of the plurality of nozzles.

Variations on any one or more of the above implementations exist, wherein depositing the selected type of nucleotide may further comprise activating an electrode in the flow cell in coordination with emitting the selected type of nucleotide from the printhead.

Variations on any one or more of the above implementations exist, wherein the flow cell may include electrodes associated with different corresponding voltages, each type of nucleotide being associated with a particular voltage. In some such implementations, the method may further comprise selecting an electrode of the electrodes, the selected electrode corresponding to the voltage associated with the selected type of nucleotide, the activated electrode being the selected electrode.

It should be appreciated that all combinations of the foregoing concepts and additional concepts discussed in greater detail below (provided such concepts are not mutually inconsistent) are contemplated as being part of the inventive subject matter disclosed herein and to achieve the benefits/advantages as described herein. In particular, all combinations of claimed subject matter appearing at the end of this disclosure are contemplated as being part of the inventive subject matter disclosed herein.

BRIEF DESCRIPTION OF THE DRAWINGS

The details of one or more implementations are set forth in the accompanying drawings and the description below. Other features, aspects, and advantages will become apparent from the description, the drawings, and the claims, in which:

Figure 1:
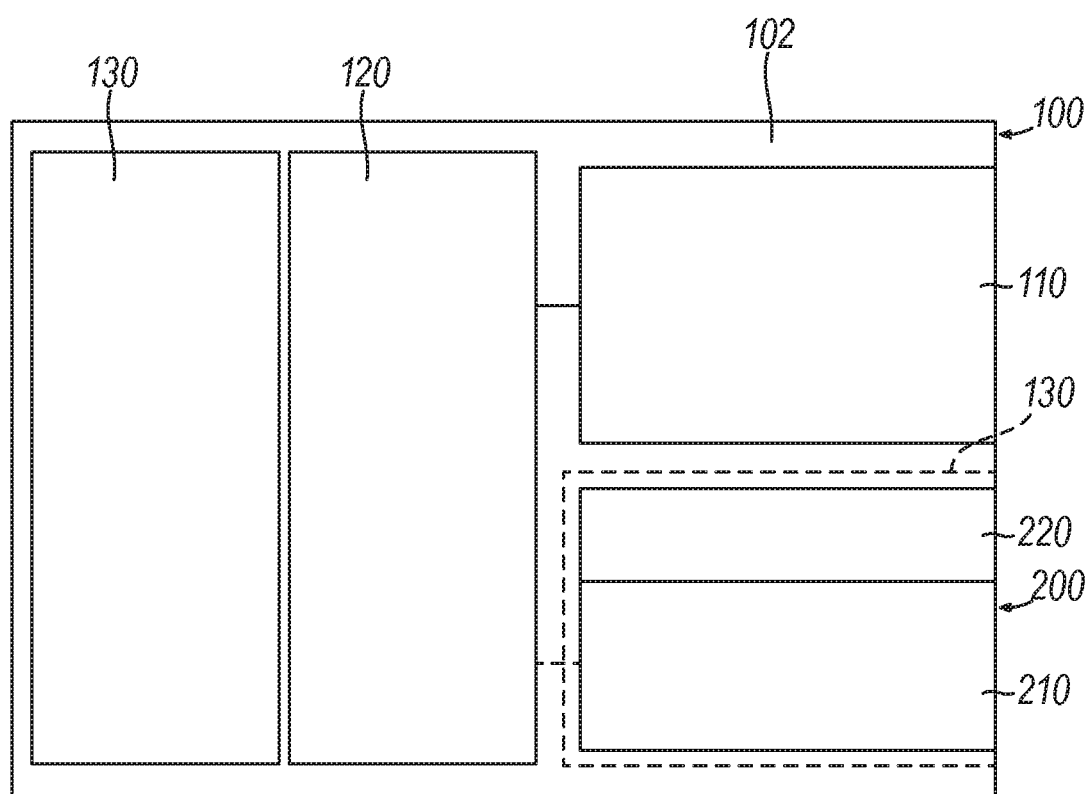
FIG. 1 depicts a block schematic view of an example of a system that may be used to conduct biochemical processes.

It will be recognized that some or all of the figures are schematic representations for purposes of illustration. The figures are provided for the purpose of illustrating one or more implementations with the explicit understanding that they will not be used to limit the scope or the meaning of the claims.

DETAILED DESCRIPTION

In some aspects, methods and systems are disclosed herein for synthesizing DNA (or other biological material) to store data or other information by selectively depositing or activating nucleotides during a writing process in a DNA storage device. Machine-written DNA may provide an alternative to traditional forms of data storage (e.g., magnetic storage, optical storage, and solid-state storage). Machine-written DNA may provide faster read-write speeds, longer data retention, reduced power usage, and higher data density.

Examples of how digital information may be stored in DNA are disclosed in U.S. Pub. No. 2015/0261664, entitled "High-Capacity of Storage of Digital Information in DNA," published Sep. 17, 2015, which is incorporated by reference herein in its entirety. For example, methods from code theory to enhance the recoverability of the encoded messages from the DNA segment, including forbidding DNA homopolymers (i.e. runs of more than one identical base) that are known to be associated with higher error rates in existing high throughput technologies may be used. Further, an error-detecting component, analogous to a parity-check bit, may be integrated into the indexing information in the code. More complex schemes, including but not limited to error-correcting codes and, indeed, substantially any form of digital data security (e.g., RAID-based schemes) currently employed in informatics, may be implemented in future developments of the DNA storage scheme. The DNA encoding of information may be computed using software. The bytes comprising each computer file may be represented by a DNA sequence with no homopolymers by an encoding scheme to produce an encoded file that replaces each byte by five or six bases forming the DNA sequence.

The code used in the encoding scheme may be constructed to permit a straightforward encoding that is close to the optimum information capacity for a run length-limited channel (e.g., no repeated nucleotides), though other encoding schemes may be used. The resulting in silico DNA sequences may be too long to be readily produced by standard oligonucleotide synthesis and may be split into overlapping segments of a length of 100 bases with an overlap of 75 bases. To reduce the risk of systematic synthesis errors introduced to any particular run of bases, alternate ones of the segments may be converted to their reverse complement, meaning that each base may be "written" four times, twice in each direction. Each segment may then be augmented with an indexing information that permits determination of the computer file from which the segment originated and its location within that computer file, plus simple error-detection information. This indexing information may also be encoded in as non-repeating DNA nucleotides and appended to the information storage bases of the DNA segments. The division of the DNA segments into lengths of 100 bases with an overlap of 75 bases is purely arbitrary and illustrative, and it is understood that other lengths and overlaps may be used and is not limiting.

Other encoding schemes for the DNA segments may be used, for example to provide enhanced error-correcting properties. The amount of indexing information may be increased in order to allow more or larger files to be encoded. One extension to the coding scheme in order to avoid systematic patterns in the DNA segments may be to add change the information. One way may use the "shuffling" of information in the DNA segments, where the information may be retrieved if one knows the pattern of shuffling. Different patterns of shuffles may be used for different ones of the DNA segments. A further way is to add a degree of randomness into the information in each one of the DNA segments. A series of random digits may be used for this, using modular addition of the series of random digits and the digits comprising the information encoded in the DNA segments. The information may be retrieved by modular subtraction during decoding if one knows the series of random digits used. Different series of random digits may be used for different ones of the DNA segments The data-encoding component of each string may contain Shannon information at 5.07 bits per DNA base, which is close to the theoretical optimum of 5.05 bits per DNA base for base-4 channels with run length limited to one. The indexing implementation may permit $31^4 = 4782969$ unique data locations. Increasing the number of indexing trits (and therefore bases) used to specify file and intra-file location by just two, to 16, gives $31^6 = 43046721$ unique locations, in excess of the 16.8M that is the practical maximum for the Nested Primer Molecular Memory (NPMM) scheme.

The DNA segment designs may be synthesized in three distinct runs (with the DNA segments randomly assigned to runs) to create approx. $1.2 \times 10^7$ copies of each DNA segment design. Phosphoramidite chemistry may be used, and inkjet printing and flow cell reactor technologies in an in-situ microarray synthesis platform may be employed. The inkjet printing within an anhydrous chamber may allow the delivery of very small volumes of phosphoramidites to a confined coupling area on a 2D planar surface, resulting in the addition of hundreds of thousands of bases in parallel. Subsequent oxidation and detritylation may be carried out in a flow cell reactor. Once DNA synthesis is completed, the oligonucleotides may then be cleaved from the surface and deprotected.

Adapters may then be added to the DNA segments to enable a plurality of copies of the DNA segments to be made. A DNA segment with no adapter may require additional chemical processes to "kick start" the chemistry for the synthesis of the multiple copies by adding additional groups onto the ends of the DNA segments. Oligonucleotides may be amplified using polymerase chain reaction (PCR) methods and paired-end PCR primers, followed by bead purification and quantification. Oligonucleotides may then be sequenced to produce reads of 104 bases. The digital information decoding may then be carried out via sequencing of the central bases of each oligo from both ends and rapid computation of full-length oligos and removal of sequence reads inconsistent with the designs. Sequence reads may be decoded using computer software that exactly reverses the encoding process. Sequence reads for which the parity-check trit indicates an error or that may be unambiguously decoded or assigned to a reconstructed computer file may be discarded. Locations within every decoded file may be detected in multiple different sequenced DNA oligos, and simple majority voting may be used to resolve any discrepancies caused by the DNA synthesis or the sequencing errors.

While several examples herein are provided in the context of machine-written DNA, it is contemplated that the principles described herein may be applied to other kinds of machine-written biological material.

As used herein, the term "machine-written DNA" shall be read to include one or more strands of polynucleotides that are generated by a machine, or otherwise modified by a machine, to store data or other information. One example of the polynucleotide herein is a DNA. It is noted that while the term "DNA" in the context of DNA being read or written is used throughout this disclosure, the term is used only as a representative example of a polynucleotide and may encompass the concept of a polynucleotide. "Machine," as used herein in reference to "machine-written," may include an instrument or system specially designed for writing DNA as described in greater detail herein. The system may be non-biological or biological. In one example, the biological system may comprise, or is, a polymerase. For example, the polymerase may be terminal deoxynucleotidyl transferase (TdT). In a biological system, the process may be additionally controlled by a machine hardware (e.g., processor) or an algorithm. "Machine-written DNA" may include any polynucleotide having one or more base sequences written by a machine. While machine-written DNA is used herein as an example, other polynucleotide strands may be substituted for machine-written DNA described herein. "Machine-written DNA" may include natural bases and modifications of natural bases, including but not limited to bases modified with methylation or other chemical tags; an artificially synthesized polymer that is similar to DNA, such as peptide nucleic acid (PNA); or Morpholino DNA. "Machine-written DNA" may also include DNA strands or other polynucleotides that are formed by at least one strand of bases originating from nature (e.g., extracted from a naturally occurring organism), with a machine-written strand of bases secured thereto either in a parallel fashion or in an end-to-end fashion. In other implementations, "machine-written DNA" may be written by a biological system (e.g., enzyme) in lieu of, or in addition to, a non-biological system (e.g., the electrode machine) writing of DNA described herein. In other words, "machine-written DNA" may be written directly by a machine; or by an enzyme (e.g., polymerase) that is controlled by an algorithm and/or machine.

"Machine-written DNA" may include data that have been converted from a raw form (e.g., a photograph, a text document, etc.) into a binary code sequence using known techniques, with that binary code sequence then being converted to a DNA base sequence using known techniques, and with that DNA base sequence then being generated by a machine in the form of one or more DNA strands or other polynucleotides. Alternatively, "machine-written DNA" may be generated to index or otherwise track pre-existing DNA, to store data or information from any other source and for any suitable purpose, without necessarily requiring an intermediate step of converting raw data to a binary code.

As described in greater detail below, machine-written DNA may be written to and/or read from a reaction site. As used herein, the term "reaction site" is a localized region where at least one designated reaction may occur. A reaction site may include support surfaces of a reaction structure or substrate where a substance may be immobilized thereon. For instance, the reaction site may be a discrete region of space where a discrete group of DNA strands or other polynucleotides are written. The reaction site may permit chemical reactions that are isolated from reactions that are in adjacent reaction sites. Devices that provide machine-writing of DNA may include flow cells with wells having writing features (e.g., electrodes) and/or reading features. In some instances, the reaction site may include a surface of a reaction structure (which may be positioned in a channel of a flow cell) that already has a reaction component thereon, such as a colony of polynucleotides thereon. In some flow cells, the polynucleotides in the colony have the same sequence, being for example, clonal copies of a single stranded or double stranded template. However, in some flow cells a reaction site may contain only a single polynucleotide molecule, for example, in a single stranded or double stranded form.

A plurality of reaction sites may be randomly distributed along the reaction structure of the flow cells or may be arranged in a predetermined manner (e.g., side-by-side in a matrix, such as in microarrays). A reaction site may also include a reaction chamber, recess, or well that at least partially defines a spatial region or volume configured to compartmentalize the designated reaction. As used herein, the term "reaction chamber" or "reaction recess" includes a defined spatial region of the support structure (which is often fluidically coupled with a flow channel). A reaction recess may be at least partially separated from the surrounding environment or other spatial regions. For example, a plurality of reaction recesses may be separated from each other by shared walls. As a more specific example, the reaction recesses may be nanowells comprising an indent, pit, well, groove, cavity or depression defined by interior surfaces of a detection surface and have an opening or aperture (i.e., be open-sided) so that the nanowells may be fluidically coupled with a flow channel.

A plurality of reaction sites may be randomly distributed along the reaction structure of the flow cells or may be arranged in a predetermined manner (e.g., side-by-side in a matrix, such as in microarrays). A reaction site may also include a reaction chamber, recess, or well that at least partially defines a spatial region or volume configured to compartmentalize the designated reaction. As used herein, the term "reaction chamber" or "reaction recess" includes a defined spatial region of the support structure (which is often fluidically coupled with a flow channel). A reaction recess may be at least partially separated from the surrounding environment or other spatial regions. For example, a plurality of reaction recesses may be separated from each other by shared walls. As a more specific example, the reaction recesses may be nanowells comprising an indent, pit, well, groove, cavity or depression defined by interior surfaces of a detection surface and have an opening or aperture (i.e., be open-sided) so that the nanowells may be fluidically coupled with a flow channel.

To read the machine-written DNA, one or more discrete detectable regions of reaction sites may be defined. Such detectable regions may be imageable regions, electrical detection regions, or other types of regions that may have a measurable change in a property (or absence of change in the property) based on the type of nucleotide present during the reading process.

As used herein, the term "pixel" refers to a discrete imageable region. Each imageable region may include a compartment or discrete region of space where a polynucleotide is present. In some instances, a pixel may include two or more reaction sites (e.g., two or more reaction chambers, two or more reaction recesses, two or more wells, etc.). In some other instances, a pixel may include just one reaction site. Each pixel is detected using a corresponding detection device, such as an image sensor or other light detection device. The light detection device may be manufactured using integrated circuit manufacturing processes, such as processes used to manufacture charged-coupled devices circuits (CCD) or complementary-metal-oxide semiconductor (CMOS) devices or circuits. The light detection device may thereby include, for example, one or more semiconductor materials, and may take the form of, for example, a CMOS light detection device (e.g., a CMOS image sensor) or a CCD image sensor, another type of image sensor. A CMOS image sensor may include an array of light sensors (e.g. photodiodes). In one implementation, a single image sensor may be used with an objective lens to capture several "pixels," during an imaging event. In some other implementations, each discrete photodiode or light sensor may capture a corresponding pixel. In some implementations, light sensors (e.g., photodiodes) of one or more detection devices may be associated with corresponding reaction sites. A light sensor that is associated with a reaction site may detect light emissions from the associated reaction site. In some implementations, the detection of light emissions may be done via at least one light guide when a designated reaction has occurred at the associated reaction site. In some implementations, a plurality of light sensors (e.g., several pixels of a light detection or camera device) may be associated with a single reaction site. In some implementations, a single light sensor (e.g. a single pixel) may be associated with a single reaction site or with a group of reaction sites.

As used herein, the term "synthesis" shall be read to include processes where DNA is generated by a machine to store data or other information. Thus, machine-written DNA may constitute synthesized DNA. As used herein, the terms "consumable cartridge," "reagent cartridge," "removeable cartridge," and/or "cartridge" refer to the same cartridge and/or a combination of components making an assembly for a cartridge or cartridge system. The cartridges described herein may be independent of the element with the reaction sites, such as a flow cell having a plurality of wells. In some instances, a flow cell may be removably inserted into a cartridge, which is then inserted into an instrument. In some other implementations, the flow cell may be removably inserted into the instrument without a cartridge. As used herein, the term "biochemical analysis" may include at least one of biological analysis or chemical analysis.

The term "based on" should be understood to mean that something is determined at least in part by the thing it is indicated as being "based on." To indicate that something must necessarily be completely determined by something else, it is described as being based exclusively on whatever it is completely determined by.

The term "non-nucleotide memory" should be understood to refer to an object, device or combination of devices capable of storing data or instructions in a form other than nucleotides that may be retrieved and/or processed by a device. Examples of "non-nucleotide memory" include solid state memory, magnetic memory, hard drives, optical drives and combinations of the foregoing (e.g., magneto-optical storage elements).

The term "DNA storage device" should be understood to refer to an object, device, or combination of devices configured to store data or instructions in the form of sequences of polynucleotides such as machine-written DNA. Examples of "DNA storage devices" include flow cells having addressable wells as described herein, systems comprising multiple such flow cells, and tubes or other containers storing nucleotide sequences that have been cleaved from the surface on which they were synthesized. As used herein, the term "nucleotide sequence" or "polynucleotide sequence" should be read to include a polynucleotide molecule, as well as the underlying sequence of the molecule, depending on context. A sequence of a polynucleotide may contain (or encode) information indicative of certain physical characteristics.

Implementations set forth herein may be used to perform designated reactions for consumable cartridge preparation and/or biochemical analysis and/or synthesis of machine-written DNA.

I. System Overview

FIG. 1 is a schematic diagram of a system 100 that is configured to conduct biochemical analysis and/or synthesis. The system 100 may include a base instrument 102 that is configured to receive and separably engage a removable cartridge 200 and/or a component with one or more reaction sites. The base instrument 102 and the removable cartridge 200 may be configured to interact with each other to transport a biological material to different locations within the system 100 and/or to conduct designated reactions that include the biological material in order to prepare the biological material for subsequent analysis (e.g., by synthesizing the biological material), and, optionally, to detect one or more events with the biological material. In some implementations, the base instrument 102 may be configured to detect one or more events with the biological material directly on the removable cartridge 200. The events may be indicative of a designated reaction with the biological material. The removable cartridge 200 may be constructed according to any of the cartridges described herein.

Although the following is with reference to the base instrument 102 and the removable cartridge 200 as shown in FIG. 1, it is understood that the base instrument 102 and the removable cartridge 200 illustrate only one implementation of the system 100 and that other implementations exist. For example, the base instrument 102 and the removable cartridge 200 include various components and features that, collectively, execute several operations for preparing the biological material and/or analyzing the biological material. Moreover, although the removable cartridge 200 described herein includes an element with the reaction sites, such as a flow cell having a plurality of wells, other cartridges may be independent of the element with the reaction sites and the element with the reaction sites may be separately insertable into the base instrument 102. That is, in some instances a flow cell may be removably inserted into the removable cartridge 200, which is then inserted into the base instrument 102. In some other implementations, the flow cell may be removably inserted directly into the base instrument 102 without the removable cartridge 200. In still further implementations, the flow cell may be integrated into the removable cartridge 200 that is inserted into the base instrument 102.

In the illustrated implementation, each of the base instrument 102 and the removable cartridge 200 are capable of performing certain functions. It is understood, however, that the base instrument 102 and the removable cartridge 200 may perform different functions and/or may share such functions. For example, the base instrument 102 is shown to include a detection assembly 110 (e.g., an imaging device) that is configured to detect the designated reactions at the removable cartridge 200. In alternative implementations, the removable cartridge 200 may include the detection assembly and may be communicatively coupled to one or more components of the base instrument 102. As another example, the base instrument 102 is a "dry" instrument that does not provide, receive, or exchange liquids with the removable cartridge 200. That is, as shown, the removable cartridge 200 includes a consumable reagent portion 210 and a flow cell receiving portion 220. The consumable reagent portion 210 may contain reagents used during biochemical analysis and/or synthesis. The flow cell receiving portion 220 may include an optically transparent region or other detectible region for the detection assembly 110 to perform detection of one or more events occurring within the flow cell receiving portion 220. In alternative implementations, the base instrument 102 may provide, for example, reagents or other liquids to the removable cartridge 200 that are subsequently consumed (e.g., used in designated reactions or synthesis procedures) by the removable cartridge 200.

As used herein, the biological material may include one or more biological or chemical substances, such as nucleosides, nucleotides, nucleic acids, polynucleotides, oligonucleotides, proteins, enzymes, peptides, oligopeptides, polypeptides, antibodies, antigens, ligands, receptors, polysaccharides, carbohydrates, polyphosphates, nanopores, organelles, lipid layers, cells, tissues, organisms, and/or biologically active chemical compound(s), such as analogs or mimetics of the aforementioned species. In some instances, the biological material may include whole blood, lymphatic fluid, serum, plasma, sweat, tear, saliva, sputum, cerebrospinal fluid, amniotic fluid, seminal fluid, vaginal excretion, serous fluid, synovial fluid, pericardial fluid, peritoneal fluid, pleural fluid, transudates, exudates, cystic fluid, bile, urine, gastric fluid, intestinal fluid, fecal samples, liquids containing single or multiple cells, liquids containing organelles, fluidized tissues, fluidized organisms, viruses including viral pathogens, liquids containing multi-celled organisms, biological swabs and biological washes. In some instances, the biological material may include a set of synthetic sequences, including but not limited to machine-written DNA, which may be fixed (e.g., attached in specific wells in a cartridge) or unfixed (e.g., stored in a tube).

In some implementations, the biological material may include an added material, such as water, deionized water, saline solutions, acidic solutions, basic solutions, detergent solutions and/or pH buffers. The added material may also include reagents that will be used during the designated assay protocol to conduct the biochemical reactions. For example, added liquids may include material to conduct multiple polymerase-chain-reaction (PCR) cycles with the biological material. In other aspects, the added material may be a carrier for the biological material such as cell culture media or other buffered and/or pH adjusted and/or isotonic carrier that may allow for or preserve the biological function of the biological material.

It should be understood, however, that the biological material that is analyzed may be in a different form or state than the biological material loaded into or created by the system 100. For example, a biological material loaded into the system 100 may include whole blood or saliva or cell population that is subsequently treated (e.g., via separation or amplification procedures) to provide prepared nucleic acids. The prepared nucleic acids may then be analyzed (e.g., quantified by PCR or sequenced by SBS) by the system 100. Accordingly, when the term "biological material" is used while describing a first operation, such as PCR, and used again while describing a subsequent second operation, such as sequencing, it is understood that the biological material in the second operation may be modified with respect to the biological material prior to or during the first operation. For example, sequencing (e.g. SBS) may be carried out on amplicon nucleic acids that are produced from template nucleic acids that are amplified in a prior amplification (e.g. PCR). In this case the amplicons are copies of the templates and the amplicons are present in higher quantity compared to the quantity of the templates.

In some implementations, the system 100 may automatically prepare a sample for biochemical analysis based on a substance provided by the user (e.g., whole blood or saliva or a population of cells). However, in other implementations, the system 100 may analyze biological materials that are partially or preliminarily prepared for analysis by the user. For example, the user may provide a solution including nucleic acids that were already isolated and/or amplified from whole blood; or may provide a virus sample in which the RNA or DNA sequence is partially or wholly exposed for processing.

As used herein, a "designated reaction" includes a change in at least one of a chemical, electrical, physical, or optical property (or quality) of an analyte-of-interest. In particular implementations, the designated reaction is an associative binding event (e.g., incorporation of a fluorescently labeled biomolecule with the analyte-of-interest). The designated reaction may be a dissociative binding event (e.g., release of a fluorescently labeled biomolecule from an analyte-of-interest). The designated reaction may be a chemical transformation, chemical change, or chemical interaction. The designated reaction may also be a change in electrical properties. For example, the designated reaction may be a change in ion concentration within a solution. Some reactions include, but are not limited to, chemical reactions such as reduction, oxidation, addition, elimination, rearrangement, esterification, amidation, etherification, cyclization, or substitution; binding interactions in which a first chemical binds to a second chemical; dissociation reactions in which two or more chemicals detach from each other; fluorescence; luminescence; bioluminescence; chemiluminescence; and biological reactions, such as nucleic acid replication, nucleic acid amplification, nucleic acid hybridization, nucleic acid ligation, phosphorylation, enzymatic catalysis, receptor binding, or ligand binding. The designated reaction may also be addition or removal of a proton, for example, detectable as a change in pH of a surrounding solution or environment. An additional designated reaction may be detecting the flow of ions across a membrane (e.g., natural or synthetic bilayer membrane). For example, as ions flow through a membrane, the current is disrupted, and the disruption may be detected. Field sensing of charged tags may also be used; as may thermal sensing and other suitable analytical sensing techniques.

In particular implementations, the designated reaction includes the incorporation of a fluorescently labeled molecule to an analyte. The analyte may be an oligonucleotide and the fluorescently labeled molecule may be a nucleotide. The designated reaction may be detected when an excitation light is directed toward the oligonucleotide having the labeled nucleotide, and the fluorophore emits a detectable fluorescent signal. In alternative implementations, the detected fluorescence is a result of chemiluminescence and/or bioluminescence. A designated reaction may also increase fluorescence (or Forster) resonance energy transfer (FRET), for example, by bringing a donor fluorophore in proximity to an acceptor fluorophore, decrease FRET by separating donor and acceptor fluorophores, increase fluorescence by separating a quencher from a fluorophore or decrease fluorescence by co-locating a quencher and fluorophore.

As used herein, a "reaction component" includes any substance that may be used to obtain a designated reaction. For example, reaction components include reagents, catalysts such as enzymes, reactants for the reaction, samples, products of the reaction, other biomolecules, salts, metal cofactors, chelating agents, and buffer solutions (e.g., hydrogenation buffer). The reaction components may be delivered, individually in solutions or combined in one or more mixture, to various locations in a fluidic network. For instance, a reaction component may be delivered to a reaction chamber where the biological material is immobilized. The reaction components may interact directly or indirectly with the biological material. In some implementations, the removable cartridge 200 is preloaded with one or more of the reaction components involved in carrying out a designated assay protocol. Preloading may occur at one location (e.g. a manufacturing facility) prior to receipt of the cartridge 200 by a user (e.g. at a customer's facility). For example, the one or more reaction components or reagents may be preloaded into the consumable reagent portion 210. In some implementations, the removable cartridge 200 may also be preloaded with a flow cell in the flow cell receiving portion 220.

In some implementations, the base instrument 102 may be configured to interact with one removable cartridge 200 per session. After the session, the removable cartridge 200 may be replaced with another removable cartridge 200. In other implementations, the base instrument 102 may be configured to interact with more than one removable cartridge 200 per session. As used herein, the term "session" includes performing at least one of sample preparation and/or biochemical analysis protocol. Sample preparation may include synthesizing the biological material; and/or separating, isolating, modifying, and/or amplifying one or more components of the biological material so that the prepared biological material is suitable for analysis. In some implementations, a session may include continuous activity in which a number of controlled reactions are conducted until (a) a designated number of reactions have been conducted, (b) a designated number of events have been detected, (c) a designated period of system time has elapsed, (d) signal-to-noise has dropped to a designated threshold; (e) a target component has been identified; (f) system failure or malfunction has been detected; and/or (g) one or more of the resources for conducting the reactions has depleted. Alternatively, a session may include pausing system activity for a period of time (e.g., minutes, hours, days, weeks) and later completing the session until at least one of (a)-(g) occurs.

An assay protocol may include a sequence of operations for conducting the designated reactions, detecting the designated reactions, and/or analyzing the designated reactions. Collectively, the removable cartridge 200 and the base instrument 102 may include the components for executing the different operations. The operations of an assay protocol may include fluidic operations, thermal-control operations, detection operations, and/or mechanical operations.

A fluidic operation includes controlling the flow of fluid (e.g., liquid or gas) through the system 100, which may be actuated by the base instrument 102 and/or by the removable cartridge 200. In one example, the fluid is in liquid form. For example, a fluidic operation may include controlling a pump to induce flow of the biological material or a reaction component into a reaction chamber.

A thermal-control operation may include controlling a temperature of a designated portion of the system 100, such as one or more portions of the removable cartridge 200. By way of example, a thermal-control operation may include raising or lowering a temperature of a polymerase chain reaction (PCR) zone where a liquid that includes the biological material is stored.

A detection operation may include controlling activation of a detector or monitoring activity of the detector to detect predetermined properties, qualities, or characteristics of the biological material. As one example, the detection operation may include capturing images of a designated area that includes the biological material to detect fluorescent emissions from the designated area. The detection operation may include controlling a light source to illuminate the biological material or controlling a detector to observe the biological material.

A mechanical operation may include controlling a movement or position of a designated component. For example, a mechanical operation may include controlling a motor to move a valve-control component in the base instrument 102 that operably engages a movable valve in the removable cartridge 200. In some cases, a combination of different operations may occur concurrently. For example, the detector may capture images of the reaction chamber as the pump controls the flow of fluid through the reaction chamber. In some cases, different operations directed toward different biological materials may occur concurrently. For instance, a first biological material may be undergoing amplification (e.g., PCR) while a second biological material may be undergoing detection.

Similar or identical fluidic elements (e.g., channels, ports, reservoirs, etc.) may be labeled differently to more readily distinguish the fluidic elements. For example, ports may be referred to as reservoir ports, supply ports, network ports, feed port, etc. It is understood that two or more fluidic elements that are labeled differently (e.g., reservoir channel, sample channel, flow channel, bridge channel) do not require that the fluidic elements be structurally different. Moreover, the claims may be amended to add such labels to more readily distinguish such fluidic elements in the claims.

A "liquid," as used herein, is a substance that is relatively incompressible and has a capacity to flow and to conform to a shape of a container or a channel that holds the substance. A liquid may be aqueous-based and include polar molecules exhibiting surface tension that holds the liquid together. A liquid may also include non-polar molecules, such as in an oil-based or non-aqueous substance. It is understood that references to a liquid in the present application may include a liquid comprising the combination of two or more liquids. For example, separate reagent solutions may be later combined to conduct designated reactions.

One or more implementations may include retaining the biological material (e.g., template nucleic acid) at a designated location where the biological material is analyzed. As used herein, the term "retained," when used with respect to a biological material, includes attaching the biological material to a surface or confining the biological material within a designated space. As used herein, the term "immobilized," when used with respect to a biological material, includes attaching the biological material to a surface in or on a solid support. Immobilization may include attaching the biological material at a molecular level to the surface. For example, a biological material may be immobilized to a surface of a substrate using adsorption techniques including non-covalent interactions (e.g., electrostatic forces, van der Waals, and dehydration of hydrophobic interfaces) and covalent binding techniques where functional groups or linkers facilitate attaching the biological material to the surface. Immobilizing a biological material to a surface of a substrate may be based upon the properties of the surface of the substrate, the liquid medium carrying the biological material, and the properties of the biological material itself. In some cases, a substrate surface may be functionalized (e.g., chemically or physically modified) to facilitate immobilizing the biological material to the substrate surface. The substrate surface may be first modified to have functional groups bound to the surface. The functional groups may then bind to the biological material to immobilize the biological material thereon. In some cases, a biological material may be immobilized to a surface via a gel.

In some implementations, nucleic acids may be immobilized to a surface and amplified using bridge amplification. Another useful method for amplifying nucleic acids on a surface is rolling circle amplification (RCA), for example, using methods set forth in further detail below. In some implementations, the nucleic acids may be attached to a surface and amplified using one or more primer pairs. For example, one of the primers may be in solution and the other primer may be immobilized on the surface (e.g., 5'-attached). By way of example, a nucleic acid molecule may hybridize to one of the primers on the surface followed by extension of the immobilized primer to produce a first copy of the nucleic acid. The primer in solution then hybridizes to the first copy of the nucleic acid which may be extended using the first copy of the nucleic acid as a template. Optionally, after the first copy of the nucleic acid is produced, the original nucleic acid molecule may hybridize to a second immobilized primer on the surface and may be extended at the same time or after the primer in solution is extended. In any implementation, repeated rounds of extension (e.g., amplification) using the immobilized primer and primer in solution may be used to provide multiple copies of the nucleic acid. In some implementations, the biological material may be confined within a predetermined space with reaction components that are configured to be used during amplification of the biological material (e.g., PCR).

One or more implementations set forth herein may be configured to execute an assay protocol that is or includes an amplification (e.g., PCR) protocol. During the amplification protocol, a temperature of the biological material within a reservoir or channel may be changed in order to amplify a target sequence or the biological material (e.g., DNA of the biological material). By way of example, the biological material may experience (1) a pre-heating stage of about 95° C. for about 75 seconds; (2) a denaturing stage of about 95° C. for about 15 seconds; (3) an annealing-extension stage of about of about 59° C. for about 45 seconds; and (4) a temperature holding stage of about 72° C. for about 60 seconds. Implementations may execute multiple amplification cycles. It is noted that the above cycle describes only one particular implementation and that alternative implementations may include modifications to the amplification protocol.

The methods and systems set forth herein may use arrays having features at any of a variety of densities including, for example, at least about 10 features/cm$^2$, about 100 features/cm$^2$, about 500 features/cm$^2$, about 1,000 features/cm$^2$, about 5,000 features/cm$^2$, about 10,000 features/cm$^2$, about 50,000 features/cm$^2$, about 100,000 features/cm$^2$, about 1,000,000 features/cm$^2$, about 5,000,000 features/cm$^2$, or higher. The methods and apparatus set forth herein may include detection components or devices having a resolution that is at least sufficient to resolve individual features at one or more of these densities.

The base instrument 102 may include a user interface 130 that is configured to receive user inputs for conducting a designated assay protocol and/or configured to communicate information to the user regarding the assay. The user interface 130 may be incorporated with the base instrument 102. For example, the user interface 130 may include a touchscreen that is attached to a housing of the base instrument 102 and configured to identify a touch from the user and a location of the touch relative to information displayed on the touchscreen. Alternatively, the user interface 130 may be located remotely with respect to the base instrument 102.

II. Cartridge

The removable cartridge 200 is configured to separably engage or removably couple to the base instrument 102 at a cartridge chamber 140. As used herein, when the terms "separably engaged" or "removably coupled" (or the like)

are used to describe a relationship between a removable cartridge 200 and a base instrument 102. The term is intended to mean that a connection between the removable cartridge 200 and the base instrument 102 are separable without destroying the base instrument 102. Accordingly, the removable cartridge 200 may be separably engaged to the base instrument 102 in an electrical manner such that the electrical contacts of the base instrument 102 are not destroyed. The removable cartridge 200 may be separably engaged to the base instrument 102 in a mechanical manner such that features of the base instrument 102 that hold the removable cartridge 200, such as the cartridge chamber 140, are not destroyed. The removable cartridge 200 may be separably engaged to the base instrument 102 in a fluidic manner such that the ports of the base instrument 102 are not destroyed. The base instrument 102 is not considered to be "destroyed," for example, if only a simple adjustment to the component (e.g., realigning) or a simple replacement (e.g., replacing a nozzle) is required. Components (e.g., the removable cartridge 200 and the base instrument 102) may be readily separable when the components may be separated from each other without undue effort or a significant amount of time spent in separating the components. In some implementations, the removable cartridge 200 and the base instrument 102 may be readily separable without destroying either the removable cartridge 200 or the base instrument 102.

In some implementations, the removable cartridge 200 may be permanently modified or partially damaged during a session with the base instrument 102. For instance, containers holding liquids may include foil covers that are pierced to permit the liquid to flow through the system 100. In such implementations, the foil covers may be damaged such that the damaged container is to be replaced with another container. In particular implementations, the removable cartridge 200 is a disposable cartridge such that the removable cartridge 200 may be replaced and optionally disposed after a single use. Similarly, a flow cell of the removable cartridge 200 may be separately disposable such that the flow cell may be replaced and optionally disposed after a single use.

In other implementations, the removable cartridge 200 may be used for more than one session while engaged with the base instrument 102 and/or may be removed from the base instrument 102, reloaded with reagents, and re-engaged to the base instrument 102 to conduct additional designated reactions. Accordingly, the removable cartridge 200 may be refurbished in some cases such that the same removable cartridge 200 may be used with different consumables (e.g., reaction components and biological materials). Refurbishing may be carried out at a manufacturing facility after the cartridge 200 has been removed from a base instrument 102 located at a customer's facility.

The cartridge chamber 140 may include a slot, mount, connector interface, and/or any other feature to receive the removable cartridge 200 or a portion thereof to interact with the base instrument 102.

The removable cartridge 200 may include a fluidic network that may hold and direct fluids (e.g., liquids or gases) therethrough. The fluidic network may include a plurality of interconnected fluidic elements that are capable of storing a fluid and/or permitting a fluid to flow therethrough. Non-limiting examples of fluidic elements include channels, ports of the channels, cavities, storage modules, reservoirs of the storage modules, reaction chambers, waste reservoirs, detection chambers, multipurpose chambers for reaction and detection, and the like. For example, the consumable reagent portion 210 may include one or more reagent wells or chambers storing reagents and may be part of or coupled to the fluidic network. The fluidic elements may be fluidically coupled to one another in a designated manner so that the system 100 is capable of performing sample preparation and/or analysis.

As used herein, the term "fluidically coupled" (or like term) refers to two spatial regions being connected together such that a liquid or gas may be directed between the two spatial regions. In some cases, the fluidic coupling permits a fluid to be directed back and forth between the two spatial regions. In other cases, the fluidic coupling is uni-directional such that there is only one direction of flow between the two spatial regions. For example, an assay reservoir may be fluidically coupled with a channel such that a liquid may be transported into the channel from the assay reservoir. However, in some implementations, it may not be possible to direct the fluid in the channel back to the assay reservoir. In particular implementations, the fluidic network may be configured to receive a biological material and direct the biological material through sample preparation and/or sample analysis. The fluidic network may direct the biological material and other reaction components to a waste reservoir.

Figure 2:
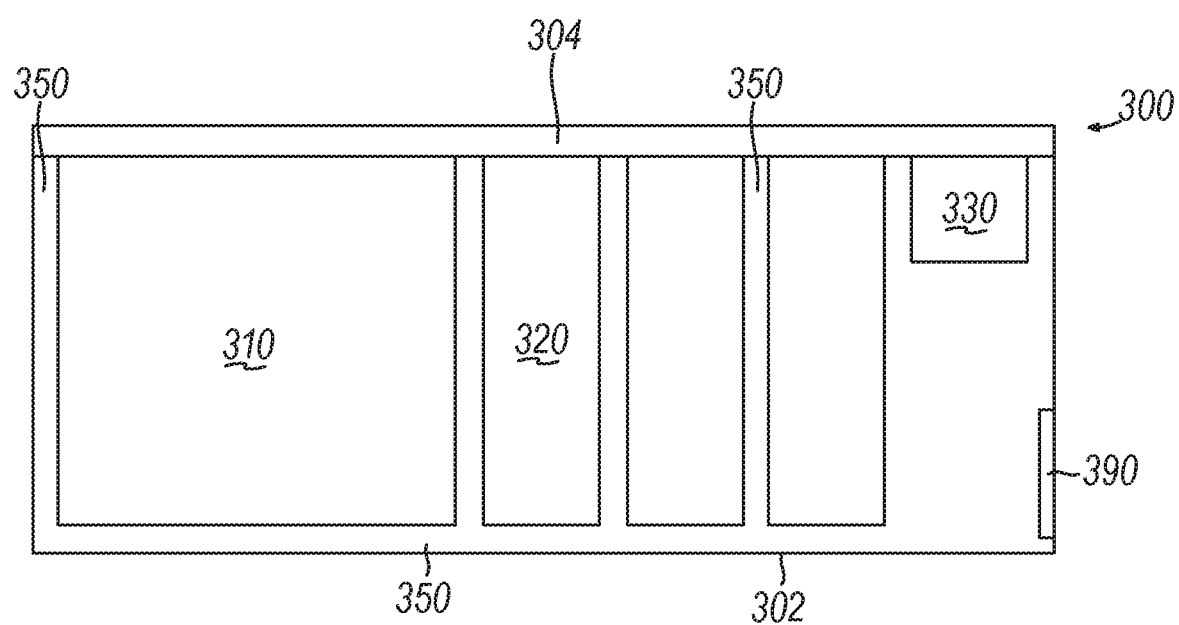
FIG. 2 depicts a block schematic cross-sectional view of an example of a consumable cartridge that may be utilized with the system of FIG. 1.

FIG. 2 depicts an implementation of a consumable cartridge 300. The consumable cartridge may be part of a combined removable cartridge, such as consumable reagent portion 210 of removable cartridge 200 of FIG. 1; or may be a separate reagent cartridge. The consumable cartridge 300 may include a housing 302 and a top 304. The housing 302 may comprise a non-conductive polymer or other material and be formed to make one or more reagent chambers 310, 320, 330. The reagent chambers 310, 320, 330 may be varying in size to accommodate varying volumes of reagents to be stored therein. For instance, a first chamber 310 may be larger than a second chamber 320, and the second chamber 320 may be larger than a third chamber 330. The first chamber 310 is sized to accommodate a larger volume of a particular reagent, such as a buffer reagent. The second chamber 320 may be sized to accommodate a smaller volume of reagent than the first chamber 310, such as a reagent chamber holding a cleaving reagent. The third chamber 330 may be sized to accommodate an even smaller volume of reagent than the first chamber 310 and the second chamber 320, such as a reagent chamber holding a fully functional nucleotide containing reagent.

In the illustrated implementation, the housing 302 has a plurality of housing walls or sides 350 forming the chambers 310, 320, 330 therein. In the illustrated implementation, the housing 302 forms a structure that is at least substantially unitary or monolithic. In alternative implementations, the housing 302 may be constructed by one or more sub-components that are combined to form the housing 302, such as independently formed compartments for chambers 310, 320, and 330.

The housing 302 may be sealed by the top 304 once reagents are provided into the respective chambers 310, 320, 330. The top 304 may comprise a conductive or non-conductive material. For instance, the top 304 may be an aluminum foil seal that is adhesively coupled to top surfaces of the housing 302 to seal the reagents within their respective chambers 310, 320, 330. In other implementations, the top 304 may be a plastic seal that is adhesively coupled to top surfaces of the housing 302 to seal the reagents within their respective chambers 310, 320, 330.

In some implementations, the housing 302 may also include an identifier 390. The identifier 390 may be a radio-frequency identification (RFID) transponder, a barcode, an identification chip, and/or other identifier. In some implementations, the identifier 390 may be embedded in the housing 302 or attached to an exterior surface. The identifier 390 may include data for a unique identifier for the consumable cartridge 300 and/or data for a type of the consumable cartridge 300. The data of the identifier 390 may be read by the base instrument 102 or a separate device configured for warming the consumable cartridge 300, as described herein.

In some implementations, the consumable cartridge 300 may include other components, such as valves, pumps, fluidic lines, ports, etc. In some implementations, the consumable cartridge 300 may be contained within a further exterior housing.

III. System Controller

The base instrument 102 may also include a system controller 120 that is configured to control operation of at least one of the removable cartridge 200 and/or the detection assembly 110. The system controller 120 may be implemented utilizing any combination of dedicated hardware circuitry, boards, DSPs, processors, etc. Alternatively, the system controller 120 may be implemented utilizing an off-the-shelf PC with a single processor or multiple processors, with the functional operations distributed between the processors. As a further option, the system controller 120 may be implemented utilizing a hybrid configuration in which certain modular functions are performed utilizing dedicated hardware, while the remaining modular functions are performed utilizing an off-the-shelf PC and the like.

The system controller 120 may include a plurality of circuitry modules that are configured to control operation of certain components of the base instrument 102 and/or the removable cartridge 200. The term "module" herein may refer to a hardware device configured to perform specific task(s). For instance, the circuitry modules may include a flow-control module that is configured to control flow of fluids through the fluidic network of the removable cartridge 200. The flow-control module may be operably coupled to valve actuators and/or s system pump. The flow-control module may selectively activate the valve actuators and/or the system pump to induce flow of fluid through one or more paths and/or to block flow of fluid through one or more paths.

The system controller 120 may also include a thermal-control module. The thermal-control module may control a thermocycler or other thermal component to provide and/or remove thermal energy from a sample-preparation region of the removable cartridge 200 and/or any other region of the removeable cartridge 200. In one particular example, a thermocycler may increase and/or decrease a temperature that is experienced by the biological material in accordance with a PCR protocol.

The system controller 120 may also include a detection module that is configured to control the detection assembly 110 to obtain data regarding the biological material. The detection module may control operation of the detection assembly 110 either through a direct wired connection or through the contact array if the detection assembly 110 is part of the removable cartridge 200. The detection module may control the detection assembly 110 to obtain data at predetermined times or for predetermined time periods. By way of example, the detection module may control the detection assembly 110 to capture an image of a reaction chamber of the flow cell receiving portion 220 of the removable cartridge when the biological material has a fluorophore attached thereto. In some implementations, a plurality of images may be obtained.

Optionally, the system controller 120 may include an analysis module that is configured to analyze the data to provide at least partial results to a user of the system 100. For example, the analysis module may analyze the imaging data provided by the detection assembly 110. The analysis may include identifying a sequence of nucleic acids of the biological material.

The system controller 120 and/or the circuitry modules described above may include one or more logic-based devices, including one or more microcontrollers, processors, reduced instruction set computers (RISC), application specific integrated circuits (ASICs), field programmable gate array (FPGAs), logic circuits, and any other circuitry capable of executing functions described herein. In an implementation, the system controller 120 and/or the circuitry modules execute a set of instructions that are stored in a computer- or machine-readable medium therein in order to perform one or more assay protocols and/or other operations. The set of instructions may be stored in the form of information sources or physical memory elements within the base instrument 102 and/or the removable cartridge 200. The protocols performed by the system 100 may be used to carry out, for example, machine-writing DNA or otherwise synthesizing DNA (e.g., converting binary data into a DNA sequence and then synthesizing DNA strands or other polynucleotides representing the binary data), quantitative analysis of DNA or RNA, protein analysis, DNA sequencing (e.g., sequencing-by-synthesis (SBS)), sample preparation, and/or preparation of fragment libraries for sequencing.

The set of instructions may include various commands that instruct the system 100 to perform specific operations such as the methods and processes of the various implementations described herein. The set of instructions may be in the form of a software program. As used herein, the terms "software" and "firmware" are interchangeable and include any computer program stored in memory for execution by a computer, including RAM memory, ROM memory, EPROM memory, EEPROM memory, and non-volatile RAM (NVRAM) memory. The above memory types are only examples and are thus not limiting as to the types of memory usable for storage of a computer program.

The software may be in various forms such as system software or application software. Further, the software may be in the form of a collection of separate programs, or a program module within a larger program or a portion of a program module. The software also may include modular programming in the form of object-oriented programming. After obtaining the detection data, the detection data may be automatically processed by the system 100, processed in response to user inputs, or processed in response to a request made by another processing machine (e.g., a remote request through a communication link).

The system controller 120 may be connected to the other components or sub-systems of the system 100 via communication links, which may be hardwired or wireless. The system controller 120 may also be communicatively connected to off-site systems or servers. The system controller 120 may receive user inputs or commands, from a user interface 130. The user interface 130 may include a keyboard, mouse, a touch-screen panel, and/or a voice recognition system, and the like.

The system controller 120 may serve to provide processing capabilities, such as storing, interpreting, and/or executing software instructions, as well as controlling the overall operation of the system 100. The system controller 120 may be configured and programmed to control data and/or power aspects of the various components. Although the system controller 120 is represented as a single structure in FIG. 1, it is understood that the system controller 120 may include multiple separate components (e.g., processors) that are distributed throughout the system 100 at different locations. In some implementations, one or more components may be integrated with the base instrument 102 and one or more components may be located remotely with respect to the base instrument 102.

IV. Flow Cell

Figure 3:
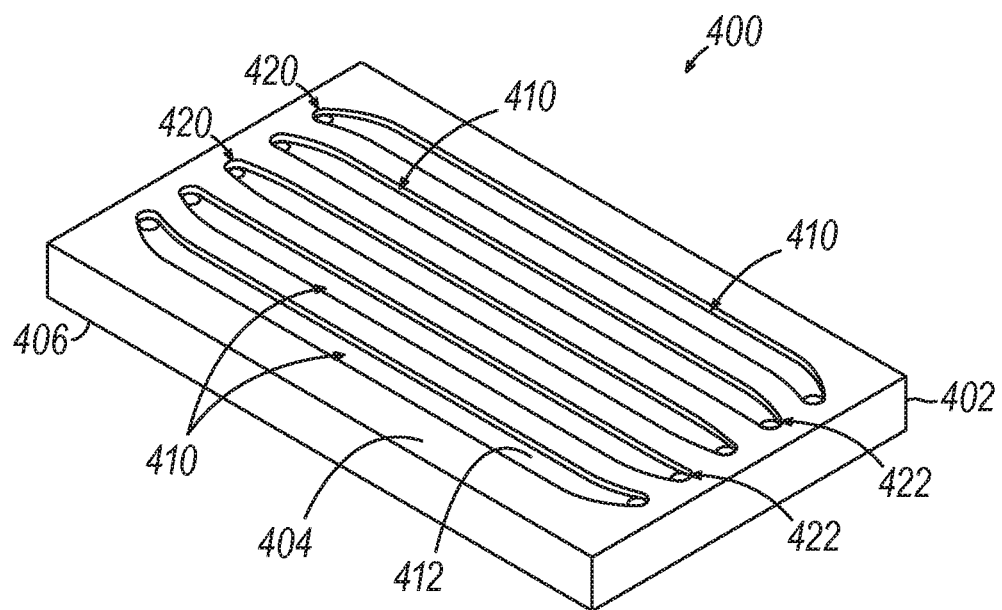
FIG. 3 depicts a perspective view of an example of a flow cell that may be utilized with the system of FIG. 1.
Figure 4:
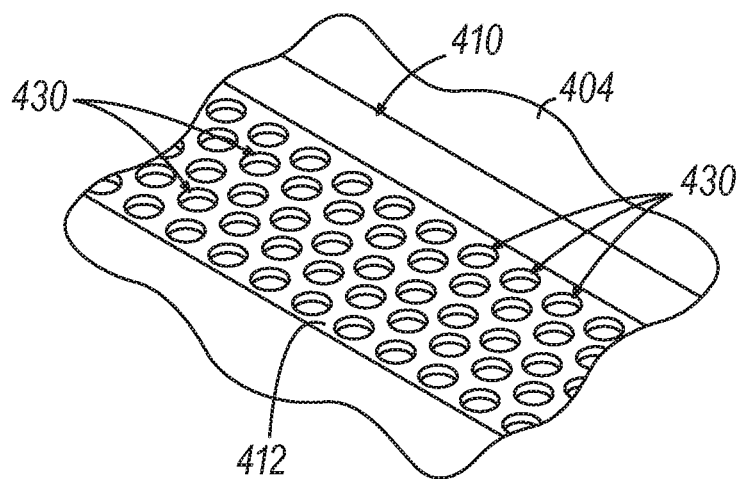
FIG. 4 depicts an enlarged perspective view of a channel of the flow cell of FIG. 3.

FIGS. 3-4 depict an example of a flow cell 400 that may be used with system 100. Flow cell of this example includes a body defining a plurality of elongate flow channels 410, which are recessed below an upper surface 404 of the body 402. The flow channels 410 are generally parallel with each other and extend along substantially the entire length of body 402. While five flow channels 410 are shown, a flow cell 400 may include any other suitable number of flow channels 410, including more or fewer than five flow channels 410. The flow cell 400 of this example also includes a set of inlet ports 420 and a set of outlet ports 422, with each port 420, 422 being associated with a corresponding flow channel 410. Thus, each inlet port 420 may be utilized to communicate fluids (e.g., reagents, etc.) to the corresponding channel 410; while each outlet port 422 may be utilized to communicate fluids from the corresponding flow channel 410.

In some versions, the flow cell 400 is directly integrated into the flow cell receiving portion 220 of the removable cartridge 200. In some other versions, the flow cell 400 is removably coupled with the flow cell receiving portion 220 of the removable cartridge 200. In versions where the flow cell 400 is either directly integrated into the flow cell receiving portion 220 or removably coupled with the flow cell receiving portion 220, the flow channels 410 of the flow cell 400 may receive fluids from the consumable reagent portion 210 via the inlet ports 420, which may be fluidly coupled with reagents stored in the consumable reagent portion 210. Of course, the flow channels 410 may be coupled with various other fluid sources or reservoirs, etc., via the ports 420, 422. As another illustrative variation, some versions of consumable cartridge 300 may be configured to removably receive or otherwise integrate the flow cell 400. In such versions, the flow channels 410 of the flow cell 400 may receive fluids from the reagent chambers 310, 320, 330 via the inlet ports 420. Other suitable ways in which the flow cell 400 may be incorporated into the system 100 will be apparent to those skilled in the art in view of the teachings herein.

FIG. 4 shows a flow channel 410 of the flow cell 400 in greater detail. As shown, the flow channel 410 includes a plurality of wells 430 formed in a base surface 412 of the flow channel 410. As will be described in greater detail below each well 430 is configured to contain DNA strands or other polynucleotides, such as machine-written polynucleotides. In some versions, each well 430 has a cylindraceous configuration, with a generally circular cross-sectional profile. In some other versions, each well 430 has a polygonal (e.g., hexagonal, octagonal, etc.) cross-sectional profile. Alternatively, wells 430 may have any other suitable configuration. It should also be understood that wells 430 may be arranged in any suitable pattern, including but not limited to a grid pattern.

Figure 5:
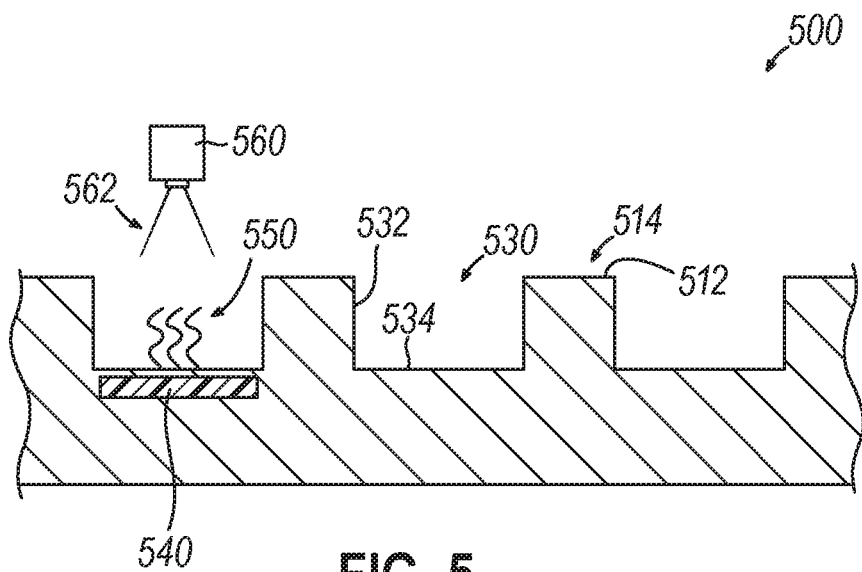
FIG. 5 depicts a block schematic cross-sectional view of an example of wells that may be incorporated into the channel of FIG. 4.

FIG. 5 shows a portion of a channel within a flow cell 500 that is an example of a variation of the flow cell 400. In other words, the channel depicted in FIG. 5 is a variation of the flow channel 410 of the flow cell 400. This flow cell 500 is operable to read polynucleotide strands 550 that are secured to the floor 534 of wells 530 in the flow cell 500. By way of example only, the floor 534 where polynucleotide strands 550 are secured may include a co-block polymer capped with azido. By way of further example only, such a polymer may comprise a poly(N-(5-azidoacetamidylpentyl)acrylamide-co-acrylamide) (PAZAM) coating provided in accordance with at least some of the teachings of U.S. Pat. No. 9,012,022, entitled "Polymer Coatings," issued Apr. 21, 2015, which is incorporated by reference herein in its entirety. Such a polymer may be incorporated into any of the various flow cells described herein.

In the present example, the wells 530 are separated by interstitial spaces 514 provided by the base surface 512 of the flow cell 500. Each well 530 has a sidewall 532 and a floor 534. The flow cell 500 in this example is operable to provide an image sensor 540 under each well 530. In some versions, each well 530 has at least one corresponding image sensor 540, with the image sensors 540 being fixed in position relative to the wells 530. Each image sensor 540 may comprise a CMOS image sensor, a CCD image sensor, or any other suitable kind of image sensor. By way of example only, each well 530 may have one associated image sensor 540 or a plurality of associated image sensors 540. As another variation, a single image sensor 540 may be associated with two or more wells 530. In some versions, one or more image sensors 540 move relative to the wells 530, such that a single image sensor 540 or single group of image sensors 540 may be moved relative to the wells 530. As yet another variation, the flow cell 500 may be movable in relation to the single image sensor 540 or single group of image sensors 540, which may be at least substantially fixed in position.

Each image sensor 540 may be directly incorporated into the flow cell 500. Alternatively, each image sensor 540 may be directly incorporated into a cartridge such as the removable cartridge 200, with the flow cell 500 being integrated into or otherwise coupled with the cartridge. As yet another illustrative variation, each image sensor 540 may be directly incorporated into the base instrument 102 (e.g., as part of the detection assembly 110 noted above). Regardless of where the image sensor(s) 540 is/are located, the image sensor(s) 540 may be integrated into a printed circuit that includes other components (e.g., control circuitry, etc.). In versions where the one or more image sensors 540 are not directly incorporated into the flow cell 500, the flow cell 500 may include optically transmissive features (e.g., windows, etc.) that allow the one or more image sensors 540 to capture fluorescence emitted by the one or more fluorophores associated with the polynucleotide strands 550 that are secured to the floors 534 of the wells 530 in the flow cell 500 as described in greater detail below. It should also be understood that various kinds of optical elements (e.g., lenses, optical waveguides, etc.) may be interposed between the floors 534 of the wells 530 and the corresponding image sensor(s) 540.

As also shown in FIG. 5, a light source 560 is operable to project light 562 into the well 530. In some versions, each well 530 has at least one corresponding light source 560, with the light sources 560 being fixed in position relative to the wells 530. By way of example only, each well 530 may have one associated light source 560 or a plurality of associated light sources 560. As another variation, a single light source 560 may be associated with two or more wells 530. In some other versions, one or more light sources 560 move relative to the wells 530, such that a single light source 560 or single group of light sources 560 may be moved relative to the wells 530. As yet another variation, the flow cell 500 may be movable in relation to the single light source 560 or single group of light sources 560, which may be substantially fixed in position. By way of example only, each light source 560 may include one or more lasers. In another example, the light source 560 may include one or more diodes.

Each light source 560 may be directly incorporated into the flow cell 500. Alternatively, each light source 560 may be directly incorporated into a cartridge such as the removable cartridge 200, with the flow cell 500 being integrated into or otherwise coupled with the cartridge. As yet another illustrative variation, each light source 560 may be directly incorporated into the base instrument 102 (e.g., as part of the detection assembly 110 noted above). In versions where the one or more light sources 560 are not directly incorporated into the flow cell 500, the flow cell 500 may include optically transmissive features (e.g., windows, etc.) that allow the wells 530 to receive the light emitted by the one or more light source 560, to thereby enable the light to reach the polynucleotide strands 550 that are secured to the floor 534 of the wells 530. It should also be understood that various kinds of optical elements (e.g., lenses, optical waveguides, etc.) may be interposed between the wells 530 and the corresponding light source(s) 560.

Figure 6:
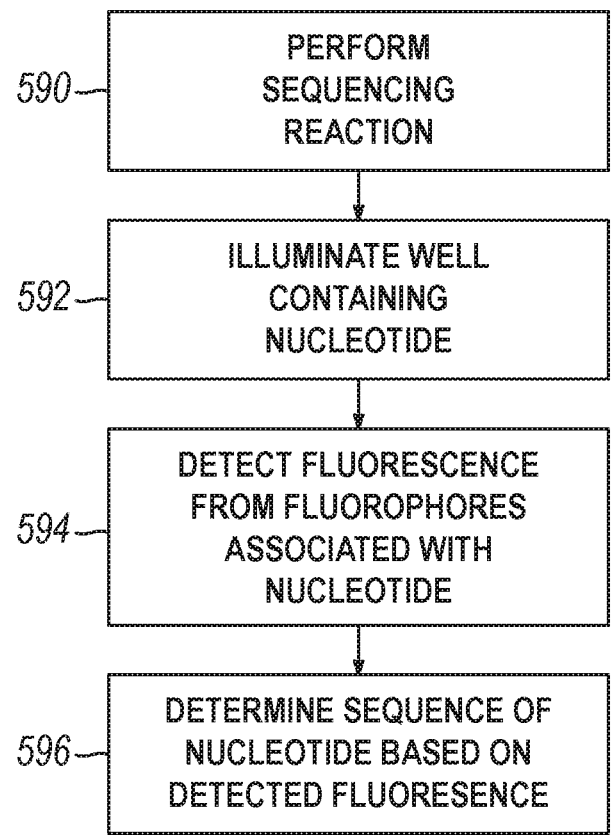
FIG. 6 depicts a flow chart of an example of a process for reading polynucleotides.

As described elsewhere herein and as is shown in block 590 of FIG. 6, a DNA reading process may begin with performing a sequencing reaction in the targeted well(s) 530 (e.g., in accordance with at least some of the teachings of U.S. Pat. No. 9,453,258, entitled "Methods and Compositions for Nucleic Acid Sequencing," issued Sep. 27, 2016, which is incorporated by reference herein in its entirety). Next, as shown in block 592 of FIG. 6, the light source(s) 560 is/are activated over the targeted well(s) 530 to thereby illuminate the targeted well(s) 530. The projected light 562 may cause a fluorophore associated with the polynucleotide strands 550 to fluoresce. Accordingly, as shown in block 594 of FIG. 6, the corresponding image sensor(s) 540 may detect the fluorescence emitted from the one or more fluorophores associated with the polynucleotide strands 550. The system controller 120 of the base instrument 102 may drive the light source(s) 560 to emit the light. The system controller 120 of the base instrument 102 may also process the image data obtained from the image sensor(s) 540, representing the fluorescent emission profiles from the polynucleotide strands 550 in the wells 530. Using this image data from the image sensor(s) 540, and as shown in block 596 of FIG. 6, the system controller 120 may determine the sequence of bases in each polynucleotide strand 550. By way of example only, this process and equipment may be utilized to map a genome or otherwise determine biological information associated with a naturally occurring organism, where DNA strands or other polynucleotides are obtained from or otherwise based on a naturally occurring organism. Alternatively, the above-described process and equipment may be utilized to obtain data stored in machine-written DNA as will be described in greater detail below.

By way of further example only, when carrying out the above-described procedure shown in FIG. 6, time space sequencing reactions may utilize one or more chemistries and imaging events or steps to differentiate between a plurality of analytes (e.g., four nucleotides) that are incorporated into a growing nucleic acid strand during a sequencing reaction; or alternatively, fewer than four different colors may be detected in a mixture having four different nucleotides while still resulting in the determination of the four different nucleotides (e.g., in a sequencing reaction). A pair of nucleotide types may be detected at the same wavelength, but distinguished based on a difference in intensity for one member of the pair compared to the other, or based on a change to one member of the pair (e.g., via chemical modification, photochemical modification, or physical modification) that causes apparent signal to appear or disappear compared to the signal detected for the other member of the pair.

V. Machine-Writing Biological Material

In some implementations, a system 100 such as the system 100 shown in FIG. 1 may be configured to synthesize biological materials (e.g. polynucleotide, such as DNA) to encode data that may later be retrieved through the performance of assays such as those described above. In some implementations, this type of encoding may be performed by assigning values to nucleotide bases (e.g., binary values, such as 0 or 1, ternary values such as 0, 1 or 2, etc.), converting the data to be encoded into a string of the relevant values (e.g., converting a textual message into a binary string using the ASCII encoding scheme), and then creating one or more polynucleotides made up of nucleotides having bases in a sequence corresponding to the string obtained by converting the data.

Figure 7:
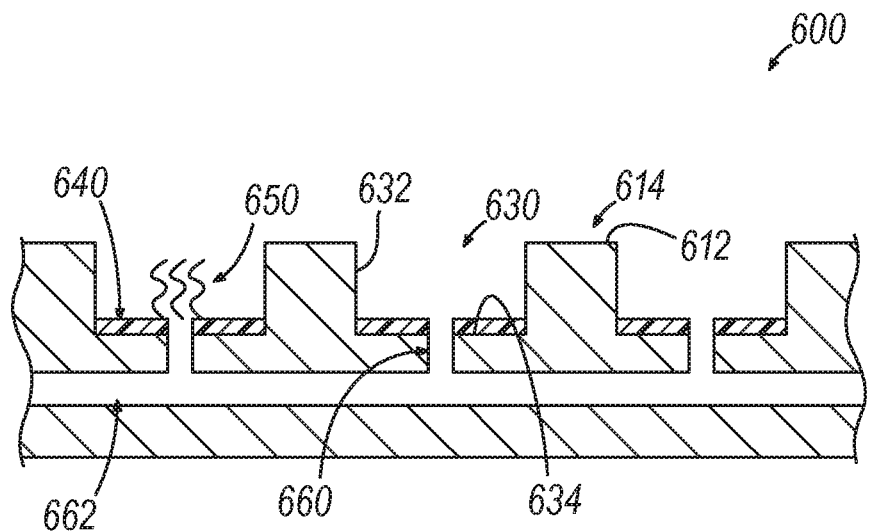
FIG. 7 depicts a block schematic cross-sectional view of another example of wells that may be incorporated into the channel of FIG. 4.

In some implementations, the creation of such polynucleotides may be performed using a version of the flow cell 400 having an array of wells 630 that are configured as shown in FIG. 7. FIG. 7 shows a portion of a channel within a flow cell 600 that is an example of a variation of the flow cell 400. In other words, the channel depicted in FIG. 7 is a variation of the flow channel 410 of the flow cell 400. In this example, each well 630 is recessed below a base surface 612 of the flow cell 600. The wells 630 are thus spaced apart from each other by interstitial spaces 614. By way of example only, the wells 630 may be arranged in a grid or any other suitable pattern along the base surface 612 of the flow cell 600. Each well 630 of this example includes a sidewall 632 and a floor 634. Each well 630 of this example further includes a respective electrode assembly 640 positioned on the floor 634 of the well 630. In some versions, each electrode assembly 640 includes just a single electrode element. In some other versions, each electrode assembly 640 includes a plurality of electrode elements or segments. The terms "electrode" and "electrode assembly" should be read herein as being interchangeable.

Base instrument 102 is operable to independently activate electrode assemblies 640, such that one or more electrode assemblies 640 may be in an activated state while one or more other electrode assemblies 640 are not in an activated state. In some versions, a CMOS device or other device is used to control electrode assemblies 640. Such a CMOS device may be integrated directly into the flow cell 600, may be integrated into a cartridge (e.g., cartridge 200) in which the flow cell 600 is incorporated, or may be integrated directly into the base instrument 102. As shown in FIG. 7, each electrode assembly 640 extends along the full width of floor 634, terminating at the sidewall 632 of the corresponding well 630. In other versions, each electrode assembly 640 may extend along only a portion of the floor 634. For instance, some versions of electrode assembly 640 may terminate interiorly relative to the sidewall 632. While each electrode assembly 540 is schematically depicted as a single element in FIG. 5, it should be understood that each electrode assembly 540 may in fact be formed by a plurality of discrete electrodes rather than just consisting of one single electrode.

As shown in FIG. 7, specific polynucleotide strands 650 may be created in individual wells 630 by activating the electrode assembly 640 of the relevant wells 630 to electrochemically generate acid that may deprotect the end group of the polynucleotide strand 650 in the well 630. By way of example only, polynucleotide strands 650 may be chemically attached to the surface at the bottom of the well 630 using linkers having chemistries such as silane chemistry on one end and DNA synthesis compatible chemistry (e.g., a short oligo for enzyme to bind to) on the other end.

To facilitate reagent exchange (e.g., transmission of a deblocking agent), each electrode assembly 640 and the floor 634 of each well 630 may include at least one opening 660 in this example. The openings 660 may be fluidly coupled with a flow channel 662 that extends underneath the wells 630, below the floors 634. To provide such an opening 660 through the electrode assembly 640, the electrode assembly 640 may be annular in shape, may be placed in quadrants, may be placed on the perimeter or sidewall 632 of the well 630, or may be placed or shaped in other suitable manners to avoid interference with reagent exchange and/or passage of light (e.g., as may be used in a sequencing process that involved detection of fluorescent emissions). In other implementations, reagents may be provided into the flow channel of the flow cell 600 without the openings 660. It should be understood that the openings 660 may be optional and may be omitted in some versions. Similarly, the flow channel 662 may be optional and may be omitted in some versions.

Figure 9:
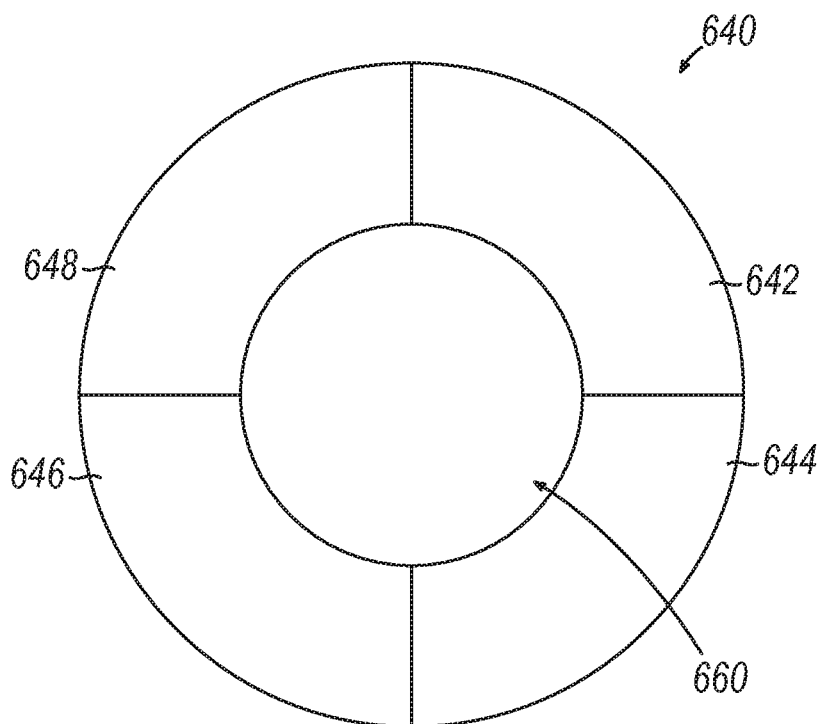
FIG. 9 depicts a top plan view of an example of an electrode assembly.

FIG. 9 shows an example of a form that electrode assembly 640 may take. In this example, electrode assembly 640 includes four discrete electrode segments 642, 644, 646, 648 that together define an annular shape. The electrode segments 642, 644, 646, 648 are thus configured as discrete yet adjacent quadrants of a ring. Each electrode segment 642, 644, 646, 648 may be configured to provide a predetermined charge that is uniquely associated with a particular nucleotide. For instance, electrode segment 642 may be configured to provide a charge that is uniquely associated with adenine; electrode segment 644 may be configured to provide a charge that is uniquely associated with cytosine; electrode segment 646 may be configured to provide a charge that is uniquely associated with guanine; and electrode segment 648 may be configured to provide a charge that is uniquely associated with thymine. When a mixture of those four nucleotides are flowed through the flow channel above the wells 630, activation of electrode segments 642, 644, 646, 648 may cause the corresponding nucleotides from that flow to adhere to the strand 650. Thus, when electrode segment 642 is activated, it may effect writing of adenine to the strand 650; when electrode segment 644 is activated, it may effect writing of cytosine to the strand 650; when electrode segment 646 is activated, it may effect writing of guanine to the strand 650; and when electrode segment 648 is activated, it may effect writing of thymine to the strand 650. This writing may be provided by the activated electrode segment 642, 644, 646, 648 hybridizing the inhibitor of the enzyme for the pixel associated with the activated electrode segment 642, 644, 646, 648. While electrode segments 642, 644, 646, 648 are shown as forming an annular shape in FIG. 9, it should be understood that any other suitable shape or shapes may be formed by electrode segments 642, 644, 646, 648. In still other implementations, a single electrode may be utilized for the electrode assembly 640 and the charge may be modulated to incorporate various nucleotides to be written to the DNA strand or other polynucleotide.

As another example, the electrode assembly 640 may be activated to provide a localized (e.g., localized within the well 630 in which the electrode assembly 640 is disposed), electrochemically generated change in pH; and/or electrochemically generate a moiety (e.g., a reducing or oxidizing reagent) locally to remove a block from a nucleotide. As yet another variation, different nucleotides may have different blocks; and those blocks may be photocleaved based on a wavelength of light communicated to the well 630 (e.g., light 562 projected from the light source 560). As still another variation, different nucleotides may have different blocks; and those blocks may be cleaved based on certain other conditions. For instance, one of the four blocks may be removed based on a combination of a reducing condition plus either high local pH or low local pH; another of the four blocks may be removed based on a combination of an oxidative condition plus either high local pH or low local pH; another of the four blocks may be removed based on a combination of light and a high local pH; and another of the four blocks may be removed based on a combination of light and a low local pH. Thus, four nucleotides may be incorporated at the same time, but with selective unblocking occurring in response to four different sets of conditions.

The electrode assembly 640 further defines the opening 660 at the center of the arrangement of the electrode segments 642, 644, 646, 648. As noted above, this opening 660 may provide a path for fluid communication between the flow channel 662 and the wells 630, thereby allowing reagents, etc. that are flowed through the flow channel 662 to reach the wells 630. As also noted above, some variations may omit the flow channel 662 and provide communication of reagents, etc. to the wells 630 in some other fashion (e.g., through passive diffusion, etc.). Regardless of whether fluid is communicated through the opening 660, the opening 660 may provide a path for optical transmission through the bottom of the well 630 during a read cycle, as described herein. In some versions, the opening 660 may be optional and may thus be omitted. In versions where the opening 660 is omitted, fluids may be communicated to the wells 630 via one or more flow channels that are above the wells 630 or otherwise positioned in relation to the wells 630. Moreover, the opening 660 may not be needed for providing a path for optical transmission through the bottom of the well 630 during a read cycle. For instance, as described below in relation to the flow cell 601, the electrode assembly 640 may comprise an optically transparent material (e.g., optically transparent conducting film (TCF), etc.), and the flow cell 600 itself may comprise an optically transparent material (e.g., glass), such that the electrode assembly 640 and the material forming the flow cell 600 may allow the fluorescence emitted from the one or more fluorophores associated with the machine-written polynucleotide strands 650 to reach an image sensor 540 that is under the well 630.

Figure 8:
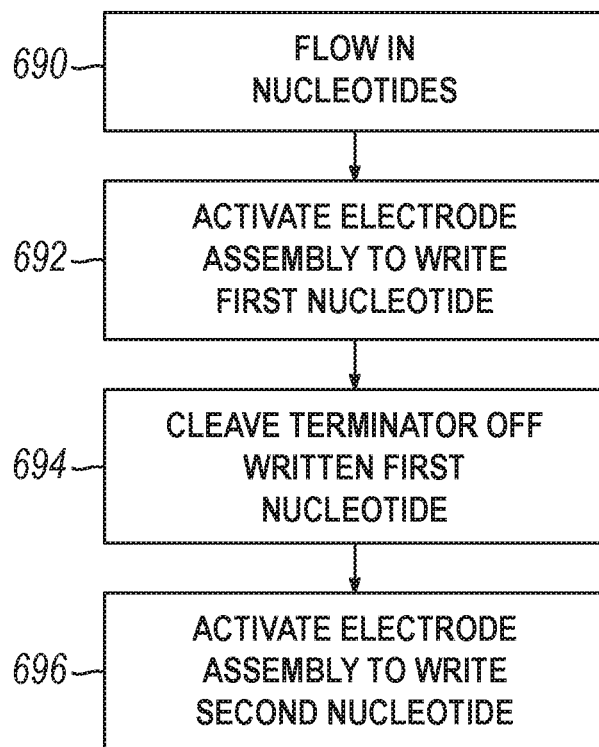
FIG. 8 depicts a flow chart of an example of a process for writing polynucleotides.

FIG. 8 shows an example of a process that may be utilized in the flow cell 600 to machine-write polynucleotides or other nucleotide sequences. At the beginning of the process, as shown in the first block 690 of FIG. 8, nucleotides may be flowed into the flow cell 600, over the wells 630. As shown in the next block 692 in FIG. 8, the electrode assembly 640 may then be activated to write a first nucleotide to a primer at the bottom of a targeted well 630. As shown in the next block 694 of FIG. 8, a terminator may then be cleaved off the first nucleotide that was just written in the targeted well 630. Various suitable ways in which a terminator may be cleaved off the first nucleotide will be apparent to those skilled in the art in view of the teachings herein. Once the terminator is cleaved off the first nucleotide, as shown in the next block 696 of FIG. 8, the electrode assembly 640 may be activated to write a second nucleotide to the first nucleotide. While not shown in FIG. 8, a terminator may be cleaved off the second nucleotide, then a third nucleotide may be written to the second nucleotide, and so on until the desired sequence of nucleotides has been written.

In some implementations, encoding of data via synthesis of biological materials such as DNA may be performed in other manners. For example, in some implementations, the flow cell 600 may lack the electrode assembly 640 altogether. For instance, deblock reagents may be selectively communicated from the flow channel 662 to the wells 630 through the openings 660. This may eliminate the need for electrode assemblies 640 to selectively activate nucleotides. As another example, an array of wells 630 may be exposed to a solution containing all nucleotide bases that may be used in encoding the data, and then individual nucleotides may be selectively activated for individual wells 630 by using light from a spatial light modulator (SLM). As another example, in some implementations individual bases may be assigned combined values (e.g., adenine may be used to encode the binary couplet 00, guanine may be used to encode the binary couplet 01, cytosine may be used to encode the binary couplet 10, and thymine may be used to encode the binary couplet 11) to increase the storage density of the polynucleotides being created. Other examples are also possible and will be immediately apparent to those skilled in the art in light of this disclosure. Accordingly, the above description of synthesizing biological materials such as DNA to encode data should be understood as being illustrative only; and should not be treated as limiting.

VI. Reading Machine-Written Biological Material

After polynucleotide strands 650 have been machine-written in one or more wells 630 of a flow cell 600, the polynucleotide strands 650 may be subsequently read to extract whatever data or other information was stored in the machine-written polynucleotide strands 650. Such a reading process may be carried out using an arrangement such as that shown in FIG. 5 and described above. In other words, one or more light sources 560 may be used to illuminate one or more fluorophores associated with the machine-written polynucleotide strands 650; and one or more image sensors 540 may be used to detect the fluorescent light emitted by the illuminated one or more fluorophores associated with the machine-written polynucleotide strands 650. The fluorescence profile of the light emitted by the illuminated one or more fluorophores associated with the machine-written polynucleotide strands 650 may be processed to determine the sequence of bases in the machine-written polynucleotide strands 650. This determined sequence of bases in the machine-written polynucleotide strands 650 may be processed to determine the data or other information that was stored in the machine-written polynucleotide strands 650.

In some versions, the machine-written polynucleotide strands 650 remain in the flow cell 600 containing wells 630 for a storage period. When it is desired to read the machine-written polynucleotide strands 650, the flow cell 600 may permit the machine-written polynucleotide strands 650 to be read directly from the flow cell. By way of example only, the flow cell 600 containing wells 630 may be received in a cartridge (e.g., cartridge 200) or base instrument 102 containing light sources 560 and/or image sensors 540, such that the machine-written polynucleotide strands 650 are read directly from the wells 630.

Figure 10:
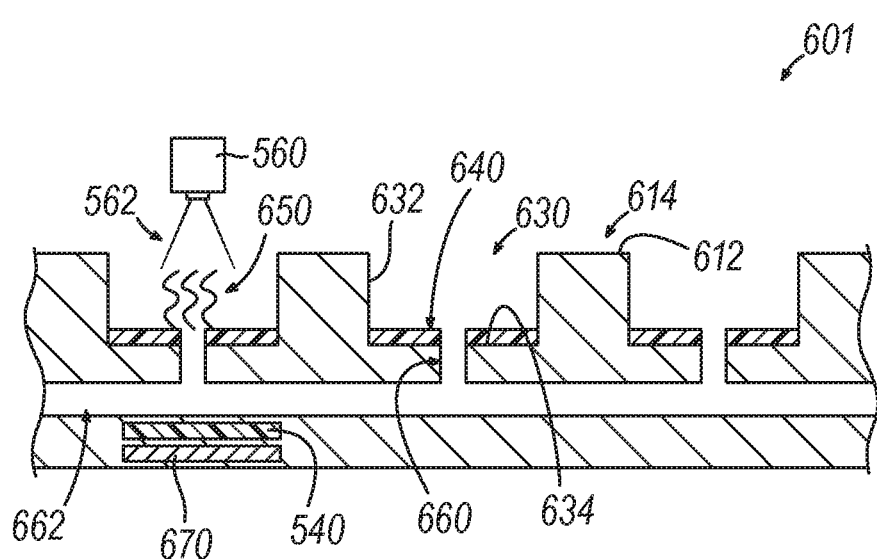
FIG. 10 depicts a block schematic cross-sectional view of another example of wells that may be incorporated into the channel of FIG. 4.

As another illustrative example, the flow cell containing wells 630 may directly incorporate one or both of light source(s) 560 or image sensor(s) 540. FIG. 10 shows an example of a flow cell 601 that includes wells 630 with electrode assemblies 640, one or more image sensors 540, and a control circuit 670. Like in the flow cell 500 depicted in FIG. 5, the flow cell 601 of this example is operable to receive light 562 projected from a light source 560. This projected light 562 may cause one or more fluorophores associated with the machine-written polynucleotide strands 650 to fluoresce; and the corresponding image sensor(s) 540 may capture the fluorescence emitted from the one or more fluorophores associated with the machine-written polynucleotide strands 650.

As noted above in the context of the flow cell 500, each well 650 of the flow cell 601 may include its own image sensor 540 and/or its own light source 560; or these components may be otherwise configured and arranged as described above. In the present example, the fluorescence emitted from the one or more fluorophores associated with the machine-written polynucleotide strands 650 may reach the image sensor 540 via the opening 660. In addition, or in the alternative, the electrode assembly 640 may comprise an optically transparent material (e.g., optically transparent conducting film (TCF), etc.), and the flow cell 601 itself may comprise an optically transparent material (e.g., glass), such that the electrode assembly 640 and the material forming the flow cell 601 may allow the fluorescence emitted from the one or more fluorophores associated with machine-written polynucleotide strands 650 to reach the image sensor 540. Moreover, various kinds of optical elements (e.g., lenses, optical waveguides, etc.) may be interposed between the wells 650 and the corresponding image sensor(s) to ensure that the image sensor 540 is only receiving fluorescence emitted from the one or more fluorophores associated with the machine-written polynucleotide strands 650 of the desired well(s) 630.

In the present example, the control circuit 670 is integrated directly into the flow cell 601. By way of example only, the control circuit 670 may comprise a CMOS chip and/or other printed circuit configurations/components. The control circuit 670 may be in communication with the image sensor(s) 540, the electrode assembly(ies) 640, and/or the light source 560. In this context, "in communication" means that the control circuit 670 is in electrical communication with image sensor(s) 540, the electrode assembly(ies) 640, and/or the light source 560. For instance, the control circuit 670 may be operable to receive and process signals from the image sensor(s) 540, with the signals representing images that are picked up by the image sensor(s) 540. "In communication" in this context may also include the control circuit 670 providing electrical power to the image sensor(s) 540, the electrode assembly(ies) 640, and/or the light source 560.

In some versions, each image sensor 540 has a corresponding control circuit 670. In some other versions, a control circuit 670 is coupled with several, if not all, of the image sensors in the flow cell 601. Various suitable components and configurations that may be used to achieve this will be apparent to those skilled in the art in view of the teachings herein. It should also be understood that the control circuit 670 may be integrated, in whole or in part, in a cartridge (e.g., removable cartridge 200) and/or in the base instrument 102, in addition to or in lieu of being integrated into the flow cell 601.

As still another illustrative example, regardless of whether a write-only flow cell like the flow cell 600 of FIG. 7 or a read-write flow cell like the flow cell 601 of FIG. 10 is used, the machine-written polynucleotide strands 650 may be transferred from wells 630 after being synthesized. This may occur shortly after the synthesis is complete, right before the machine-written polynucleotide strands 650 are to be read, or at any other suitable time. In such versions, the machine-written polynucleotide strands 650 may be transferred to a read-only flow cell like the flow cell 500 depicted in FIG. 5; and then be read in that read-only flow cell 500. Alternatively, any other suitable devices or processes may be used.

In some implementations, reading data encoded through the synthesis of biological materials may be achieved by determining the well(s) 630 storing the synthesized strand(s) 650 of interest and then sequencing those strands 650 using techniques such as those described previously (e.g., sequencing-by-synthesis). In some implementations, to facilitate reading data stored in nucleotide sequences, when data is stored, an index may be updated with information showing the well(s) 630 where the strand(s) 650 encoding that data was/were synthesized. For example, when an implementation of a system 100 configured to synthesize strands 650 capable of storing up to 256 bits of data is used to store a one megabit (1,048,576 bit) file, the system controller 120 may perform steps such as: 1) break the file into 4,096 256 bit segments; 2) identify a sequence of 4,096 wells 630 in the flow cell 600, 601 that were not currently being used to store data; 3) write the 4,096 segments to the 4,096 wells 430, 530; 4) update an index to indicate that the sequence starting with the first identified well 630 and ending at the last identified well 630 was being used to store the file. Subsequently, when a request to read the file was made, the index may be used to identify the well(s) 630 containing the relevant strand(s) 650, the strand(s) 650 from those wells 630 may be sequenced, and the sequences may be combined and converted into the appropriate encoding format (e.g., binary), and that combined and converted data may then be returned as a response to the read request.

In some implementations, reading of data previously encoded via synthesis of biological materials may be performed in other manners. For example, in some implementations, if a file corresponding to 4,096 wells 630 was to be written, rather than identifying 4,096 sequential wells 630 to write it to, a controller may identify 4,096 wells 630 and then update the index with multiple locations corresponding to the file in the event that those wells 630 did not form a continuous sequence. As another example, in some implementations, rather than identifying individual wells 630, a system controller 120 may group wells 630 together (e.g., into groups of 128 wells 630), thereby reducing the overhead associated with storing location data (i.e., by reducing the addressing requirements from one address per well 630 to one address per group of wells 630). As another example, in implementations that store data reflecting the location of wells 630 where DNA strands or other polynucleotides have been synthesized, that data may be stored in various ways, such as sequence identifiers (e.g., well 1, well 2, well 3, etc.) or coordinates (e.g., X and Y coordinates of a well's location in an array).

As another example, in some implementations, rather than reading strands 650 from the wells 630 in which they were synthesized, strands 650 may be read from other locations. For instance, strands 650 may be synthesized to include addresses, and then cleaved from the wells 630 and stored in a tube for later retrieval, during which the included address information may be used to identify the strands 650 corresponding to particular files. As another illustrative example, the strands 650 may be copied off the surface using polymerase and then eluted & stored in tube. Alternatively, the strands 650 may be copied on to a bead using biotinylated oligos hybridized to DNA strands or other polynucleotides and capturing extended products on streptavidin beads that are dispensed in the wells 630. Other examples are also possible and will be immediately apparent to those of skill in the art in light of this disclosure. Accordingly, the above description of retrieving data encoded through the synthesis of biological materials should be understood as being illustrative only; and should not be treated as limiting.

Implementations described herein may utilize a polymer coating for a surface of a flow cell, such as that described in U.S. Pat. No. 9,012,022, entitled "Polymer Coatings," issued Apr. 21, 2015, which is incorporated by reference herein in its entirety. Implementations described herein may utilize one or more labelled nucleotides having a detectable label and a cleavable linker, such as those described in U.S. Pat. No. 7,414,116, entitled "Labelled Nucleotide Strands," issued Aug. 19, 2008, which is incorporated by reference herein in its entirety. For instance, implementations described herein may utilize a cleavable linker that is cleavable with by contact with water-soluble phosphines or water-soluble transition metal-containing catalysts having a fluorophore as a detectable label. Implementations described herein may detect nucleotides of a polynucleotide using a two-channel detection method, such as that described in U.S. Pat. No. 9,453,258, entitled "Methods and Compositions for Nucleic Acid Sequencing," issued Sep. 27, 2016, which is incorporated by reference herein in its entirety. For instance, implementations described herein may utilize a fluorescent-based SBS method having a first nucleotide type detected in a first channel (e.g., dATP having a label that is detected in the first channel when excited by a first excitation wavelength), a second nucleotide type detected in a second channel (e.g., dCTP having a label that is detected in a second channel when excited by a second excitation wavelength), a third nucleotide type detected in both the first and second channel (e.g., dTTP having at least one label that is detected in both channels when excited by the first and/or second excitation wavelength), and a fourth nucleotide type that lacks a label that is not, or that is minimally, detected in either channel (e.g., dGTP having no label). Implementations of the cartridges and/or flow cells described herein may be constructed in accordance with one or more teachings described in U.S. Pat. No. 8,906,320, entitled "Biosensors for Biological or Chemical Analysis and Systems and Methods for Same," issued Dec. 9, 2014, which is incorporated by reference herein in its entirety; U.S. Pat. No. 9,512,422, entitled "Gel Patterned Surfaces," issued Dec. 6, 2016, which is incorporated by reference herein in its entirety; U.S. Pat. No. 10,254,225, entitled "Biosensors for Biological or Chemical Analysis and Methods of Manufacturing the Same," issued Apr. 9, 2019, which is incorporated by reference herein in its entirety; and/or U.S. Pub. No. 2018/0117587, entitled "Cartridge Assembly," published May 3, 2018, which is incorporated by reference herein in its entirety.

VII. Features for Providing Selective Deposition or Activation of Nucleotides During Writing Process in DNA Storage Device When machine-writing polynucleotides in a DNA storage device, it is desirable to provide substantial precision in the selection and activation or deposition of nucleotides in a given polynucleotide. This includes selecting the appropriate nucleotide at the appropriate moment in time; and ensuring that the selected nucleotide gets deposited at the appropriate location at the appropriate moment in time. As described herein, when performing machine-writing of polynucleotides, a solution containing all four nucleotides may be flowed through a cell; and by coupling one or more of changes in voltage, changes in pH, or light sensitivity together, a particular nucleotide in the solution may "activated" such that it attaches to a primer or existing polynucleotide in a well of a flow cell. The following provides several illustrative examples of how this process may be carried out with substantial precision.

A. Flow Cell with pH and Photonic Activation of Nucleotides

In addition to, or in lieu of, using electrodes like those of an electrode assembly 640 to selectively activate nucleotides to effect machine-writing of polynucleotides, another option is to utilize changes in pH and/or light to provide selective activation. For instance, all reagents may be provided together, and a reaction may occur only when the pH value and light value simultaneously reach certain targets. Some nucleotides may also be photoactivated, without involving the pH to reach a certain target. In addition, or in the alternative, some nucleotides may be activated in response to exposure to certain pH values, without involving a particular illumination profile for activation.

Figure 11:
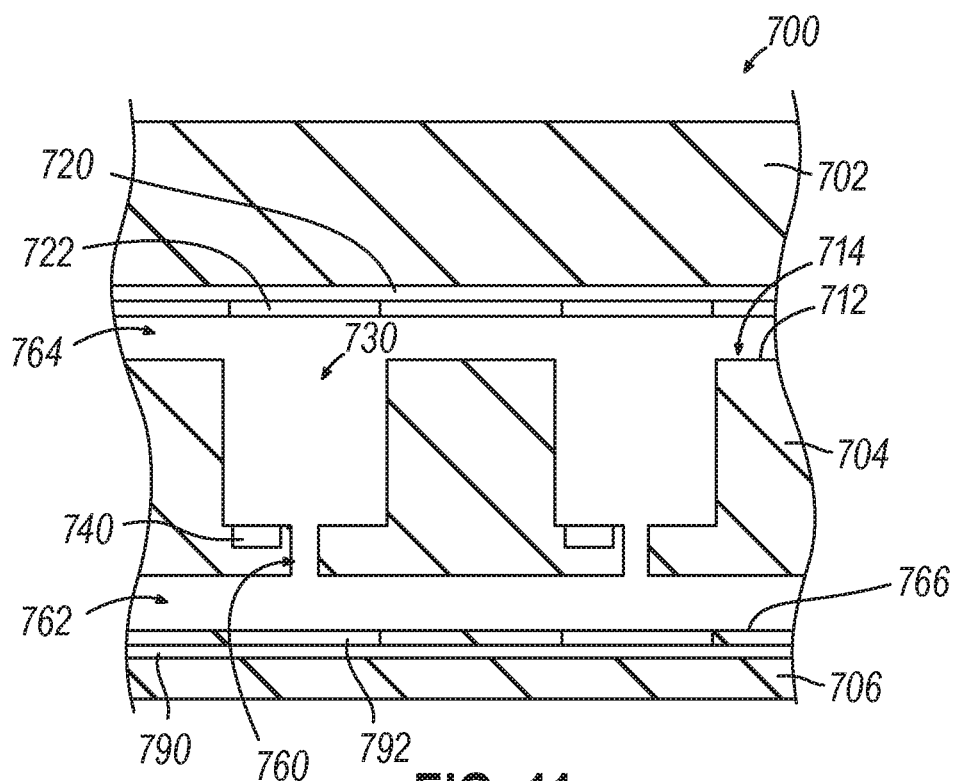
FIG. 11 depicts a block schematic cross-sectional view of another example of a flow cell that may be utilized with the system of FIG. 1.

FIG. 11 shows another example of a flow cell 700 that may be used to read and write polynucleotides as described herein, providing writing capabilities based on changes in pH and/or illumination profiles. The flow cell 700 of this example includes an upper body portion 702, a middle body portion 704, and a lower body portion 706. An upper fluid flow channel 764 is defined between the upper and middle body portions 802, 804 and is operable to receive a flow of fluid (e.g., a fluid containing nucleotide bases, etc.). A lower fluid flow channel 762 is defined between the middle and lower body portions 704, 706 and is operable to receive a separate flow of fluid (e.g., a fluid containing deblocking/deshielding agents, etc.). As with lower fluid flow channel 662 described above, lower fluid flow channel 762 of this example may be optional and may be omitted in some variations.

The flow cell 700 of this example further includes a plurality of wells 730 that are formed as recesses in the bottom surface 712 of the upper fluid flow channel 764. These wells 730 are substantially similar to the wells 630 described above. The flow cell 700 further defines a plurality of interstitial spaces 714 between the wells 730. A pH control feature 740 is positioned at the bottom of each well 730. Each well 730 lacks an electrode assembly in this example. In some other variations, each well 730 may include an electrode assembly similar to the electrode assembly 640 described above. In such variations, the pH control feature 740 and the electrode assembly may both be positioned at the bottom of each well; one may be positioned at the bottom of the well 730 while the other is positioned at the sidewall of the well 730; or any other suitable positioning may be used.

The pH control feature 740 of the present example is operable to adjust the pH level within the well 730. By way of example only, the pH control feature may comprise a bubble generator, a set of electrodes, or some other feature. The flow cell 700 may be configured to include one or more pH control features 740 to simultaneously provide pH levels that differ among different wells 730.

The pH control feature 740 may be selectively activated by a controller that is directly integrated into the flow cell 700. By way of example only, such an integrated controller may be incorporated into a CMOS chip. In some such versions, the same CMOS chip or other controller also controls other features of the flow cell 700 (e.g., the light sources 722, the image sensors 792, etc.). As another illustrative alternative, the pH control feature 740 may be selectively activated by a controller that is directly integrated into a cartridge (e.g., the removable cartridge 200) that receives the flow cell 700. As still another illustrative alternative, the pH control feature 700 may be selectively activated by a controller that is directly integrated into the base instrument 102. Moreover, components of the controller that selectively activates the pH control feature 740 may be distributed among two or more of the flow cell 700, a cartridge that receives the flow cell 700, or the base instrument 102. Various suitable components and arrangements that may be utilized to provide control of the pH control feature 740 will be apparent to those skilled in the art in view of the teachings herein. Examples of how the pH control feature 740 may be utilized during a DNA machine-writing process will be described in greater detail below.

In the present example, bottom of each well 730 includes an opening 760 providing a pathway for fluid communication between the well 730 and the lower fluid flow channel 762. In some versions, this opening 760 includes a valve that is operable to selectively open or close to thereby selectively permit or prevent fluid communication from the lower fluid flow channel 762 to the corresponding well 730. As noted above, the lower fluid flow channel 762 may be optional. Likewise, the opening 760 (and corresponding valve, if any) is also optional. Some variations of the flow cell 700 may lack the opening 760 at the bottom of each well 730.

As described above, light may be utilized to read machine-written polynucleotides within the wells 730. To that end, FIG. 11 shows a set of light sources 722 that are configured to emit light toward corresponding wells 730. While each well 730 has a corresponding light source 722 in this example, other variations may provide a light source 722 that spans across more than one well 730. The light sources 722 are all coupled with an upper integrated circuit layer 720 and are positioned to be flush with the upper surface 724 of the upper flow channel 726 in this example. Alternatively, the light sources 722 may have some other relationship with the upper surface 724 of the upper flow channel 726. The upper integrated circuit layer 720 is operable to selectively drive the light sources 722 independently of each other.

By way of example only, the upper integrated circuit layer 720 may include a CMOS chip. By way of further example only, the light sources 722 may include microscopic light emitting diodes (microLEDs) that are integrated in a CMOS chip that is part of the upper integrated circuit layer 720. Alternatively, the light sources 720 (regardless of whether they include microLEDs) may otherwise be coupled with the upper integrated circuit layer 720. In some versions, each light source 722 for each well 730 consists of a single microLED. In some other versions, each light source 722 for each well 730 consists of an array of microLEDs. Alternatively, any other suitable kind of light source may be used for light sources 722.

The flow cell 700 of the present example further includes a lower integrated circuit layer 790 with a plurality of image sensors 792. By way of example only, the lower integrated circuit layer 790 and image sensors 792 may be part of a CMOS chip. The lower integrated circuit layer 790 and image sensors 792 are integrated into the lower body portion 706 in this example, with the image sensors 792 being positioned at the lower surface 866 of the lower fluid flow channel 762. In some other variations, the lower integrated circuit layer 790 and image sensors 792 are integrated into some other component. By way of example only, the lower integrated circuit layer 790 and/or image sensors 792 may be integrated into a cartridge (e.g., the removable cartridge 200) that receives the flow cell 700; may be integrated into the base instrument 102; or may be integrated in some other component. The lower integrated circuit layer 790 and image sensors 792 are in communication with each other. In this context, "in communication" means that the lower integrated circuit layer 790 is in electrical communication with the image sensors 792. For instance, the lower integrated circuit layer 790 may be operable to receive and process signals from the image sensors 792, with the signals representing images that are picked up by the image sensors 792. "In communication" in this context may also include the lower integrated circuit layer 790 providing electrical power to the image sensors 792.

Each image sensor 792 is positioned under a corresponding well 730. Thus, when light source(s) 722 is/are activated to emit light toward the well(s) 730, the corresponding image sensor(s) 792 is/are configured to detect fluorescence emitted by fluorophores associated with polynucleotides (e.g., machine-written DNA) contained within the well(s) 730. The fluorescent light profile detected by image sensors 792 may be utilized to read the polynucleotides as described herein. In some other variations of the flow cell 700, the image sensors 792 are omitted. In some such versions, the flow cell 700 is a "write only" flow cell. In some other versions where the image sensors 792 are omitted, the image sensors are provided by some other piece of equipment (e.g., the removable cartridge 200, the base instrument 102, etc.).

As noted above, nucleotides may be selectively activated or deposited based on exposure to a medium having a particular pH value and/or based on exposure to light having a certain frequency. By way of example only, modified nucleotides may have incorporation blockers that may be deblocked by a combination of pH and light. For instance, where a flow cell 700 may control pH between two values and control light between two values, the flow cell 700 may selectively deblock the incorporation blocker of a given nucleotide, thereby making the nucleotide capable of incorporation by an enzyme. One example of a type of incorporation blocker may include a chemical moiety that prevents the blocked modified nucleotide from entering the active pocket of the enzyme. In some instances, the modified nucleotide may also include an extension blocker.

To achieve selective activation or deposition as described above, the flow cell 700 may selectively activate the light sources 722 and/or the pH control feature 740. For instance, if a particular nucleotide base requires exposure to a certain pH value in combination with exposure to light at a certain frequency, and if it desirable to add that nucleotide base to a polynucleotide in a given well 730, the pH control feature 740 and light source 722 of that well 730 may be driven to provide that particular combination of pH value and light frequency to thereby activate/deposit that particular nucleotide base. To complete a machine-written polynucleotide in a given well 730, the flow cell 700 may selectively drive the pH control feature 740 and light source 722 for that well 730 to provide a particular sequence of pH values and light frequencies in accordance with a desired corresponding sequence of nucleotide bases to thereby attach those nucleotide bases to a primer at the bottom of the well 730 in the desired sequence.

In the foregoing example, the flow cell 700 provides selective activation/deposition of nucleotide bases based on a combination of pH values and light frequencies associated with particular nucleotide bases. In some other versions, the flow cell 700 provides selective activation/deposition of nucleotide bases based solely on pH values associated with particular nucleotide bases. In such versions, the flow cell 700 drives the pH control feature 740 for a given well 730 to provide a particular sequence of pH values in accordance with a desired corresponding sequence of nucleotide bases to thereby attach those nucleotide bases to a primer at the bottom of the well 730 in the desired sequence. In such versions, the light source 722 may be used solely for a reading stage or may be omitted altogether.

As yet another illustrative variation, the flow cell 700 may provide selective activation/deposition of nucleotide bases based solely on light frequencies associated with particular nucleotide bases. In such versions, the flow cell 700 drives the light source 722 for a given well 730 to provide a particular sequence of light frequencies in accordance with a desired corresponding sequence of nucleotide bases to thereby attach those nucleotide bases to a primer at the bottom of the well 730 in the desired sequence. In such versions, pH control feature 740 may be omitted altogether.

It should be understood from the foregoing that, in versions of the flow cell 700 that include light sources 722, such light sources 722 may be utilized both during a writing stage (e.g., when light frequencies alone or in combination with pH values cause selective activation/deposition of nucleotides) and during a reading stage (e.g., similar to light source 560 described above in the context of flow cells 500, 601). Alternatively, two separate light sources may be used—one that is only used during a writing stage and another that is used only during a reading stage. As yet another illustrative alternative, the flow cell 700 may be a "write only" flow cell where the image sensors 792 are omitted such that the light sources 722 are only used during a writing process.

B. Flow Cell with Illumination Assembly for Activation of Nucleotides

Figure 12:
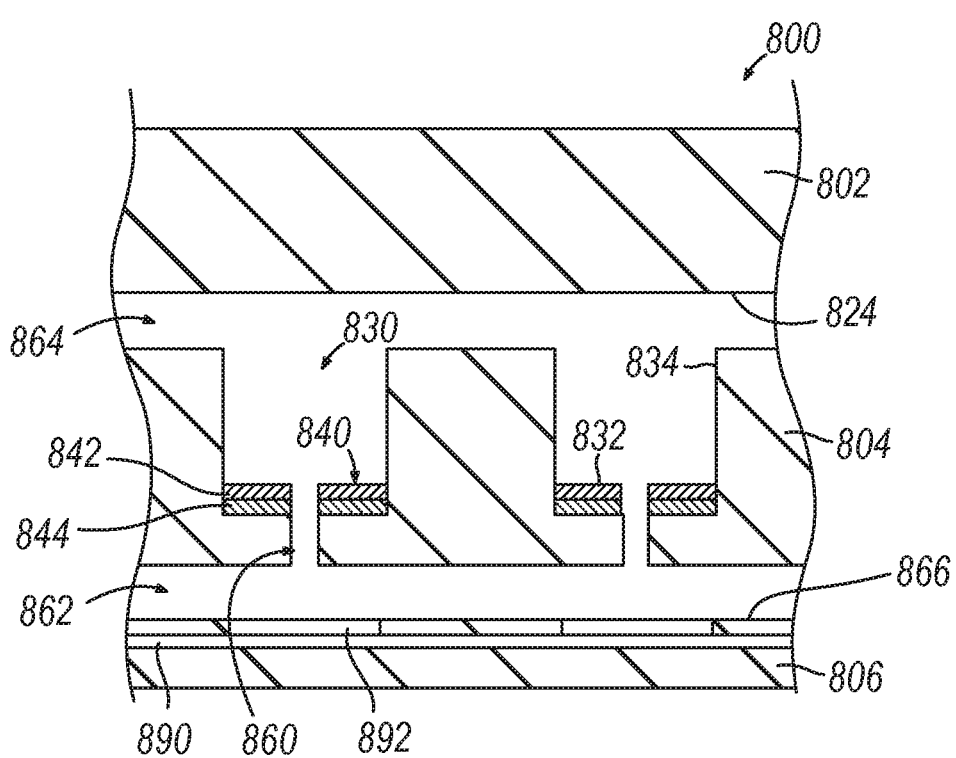
FIG. 12 depicts a block schematic cross-sectional view of another example of a flow cell that may be utilized with the system of FIG. 1.

As noted above, light (alone or in combination with pH values) may be utilized to selectively activate or deposit nucleotides. For instance, different nucleotides may be activated or deposited in response to exposure to different light frequencies. FIG. 12 shows another example of a flow cell 800 that may be utilized to provide machine-writing of polynucleotides by providing selectively activated sequences of light frequencies to thereby selectively activate corresponding nucleotide bases during a DNA machine-writing process.

The flow cell 800 of the example shown in FIG. 12 includes an upper body portion 802, a middle body portion 804, and a lower body portion 806. An upper fluid flow channel 864 is defined between the upper and middle body portions 802, 804 and is operable to receive a flow of fluid (e.g., a fluid containing nucleotide bases, etc.). A lower fluid flow channel 862 is defined between the middle and lower body portions 804, 806 and is operable to receive a separate flow of fluid (e.g., a fluid containing deblocking/deshielding agents, etc.). As with lower fluid flow channel 662 described above, lower fluid flow channel 862 of this example may be optional and may be omitted in some variations.

The flow cell 800 of this example further includes a plurality of wells 830 that are formed as recesses in the bottom surface of the upper fluid flow channel 864. These wells 830 are at least substantially similar to the wells 630 described above. An illumination assembly 840 is positioned at the bottom 832 of each well 830. The illumination assembly 840 includes a microLED panel 844 and a polarizer grid 842 laid over the microLED panel 842. By way of example only, each microLED panel 844 may include a plurality of microLEDs arranged in a grid or other pattern, with each microLED being operable to emit light at a particular frequency. While the microLED panel 844 is located at the bottom 832 of each well 830 in this example, the microLED panel 844 may instead be located elsewhere. For instance, the microLED panel 844 may instead be located in or on the sidewall 834 of each well 830. As another illustrative alternative, each microLED panel 844 may be located on or in the upper surface 824 of the upper flow channel 824, directly above the corresponding well 830. In versions where the microLED panel 844 is located in or on the sidewall 834, or on or in the upper surface 824, each polarizer grid 842 may be correspondingly located or may be omitted.

The polarizer grid 842 may include an array of polarizing elements that may be selectively activated to serve as shutters over corresponding microLEDs of the microLED panel 844. In other words, the number and arrangement of polarizing elements in the polarizer grid 842 may correspond directly with the number and arrangement of microLEDs in the microLED panel 844. The polarizing grid 842 may be activated to permit light emitted by a selected microLED of the microLED panel 844 to only reach a corresponding region of the surface area at the bottom of the well 830. To achieve this, the polarizing grid 842 may effectively "open" only the "shutter" provided by the polarizing element that is directly over the activated microLED of the microLED panel 844, leaving the rest of the "shutters" provided by the rest of the polarizing elements in a "closed" state. This may provide greater precision in the delivery of light to the bottom surface of the well 830, preventing the light from undesirably reaching regions of the bottom surface of the well 830 that are adjacent to the targeted region. It should be understood that the polarizing grid 842 may be optional. Other variations of the flow cell 800 may lack the polarizing grid 842.

In the present example, the bottom 832 of each well 830 also includes an opening 860 providing a pathway for fluid communication between the well 830 and the lower fluid flow channel 862. In some versions, this opening 860 includes a valve that is operable to selectively open or close to thereby selectively permit or prevent fluid communication from the lower fluid flow channel 862 to the corresponding well 830. As noted above, the lower fluid flow channel 862 may be optional. Likewise, the opening 860 (and corresponding valve, if any) may be optional. Some variations of the flow cell 800 may lack the opening 860 at the bottom of each well 830.

As described above, light may be utilized to machine-write polynucleotides. In particular, nucleotides may be selectively activated or deposited based on exposure to light having a certain frequency. To achieve this activation/deposition, the flow cell 800 may selectively activate the illumination assembly 840. For instance, if a particular nucleotide base requires exposure to light at a certain frequency, and if it desirable to add that nucleotide base to a polynucleotide in a given well 830, the illumination assembly 840 of that well 830 may be driven to provide that particular light frequency at a particular region on the bottom 832 of the well 830 to thereby activate/deposit that particular nucleotide base at that particular region. To complete a machine-written polynucleotide in a given well 830, the flow cell 800 may selectively drive the illumination assembly 840 for that well 830 to provide a particular sequence of light frequencies in accordance with a desired corresponding sequence of nucleotide bases to thereby attach those nucleotide bases to a primer at the corresponding region of the bottom 832 of the well 830 in the desired sequence.

While the flow cell 800 of this example lacks a pH control feature like the pH control feature 740 of the flow cell 700 described above with reference to FIG. 11, other variations of the flow cell 800 of FIG. 12 may include a pH control feature like the pH control feature 740 of the flow cell 700. Such a pH control feature may be operated in cooperation with the illumination assembly 840 to selectively activate/deposit nucleotide bases based on a combination of pH values and light frequencies associated with particular nucleotide bases.

As also described above, light may be utilized to read machine-written polynucleotides within the wells 830. To that end, the same illumination assemblies 840 that are used to provide machine-writing of polynucleotides may be used to provide reading of machine-written polynucleotides. In other words, the microLED panel 844 may be activated to illuminate machine-written polynucleotides in a corresponding well 830, and fluorophores associated with those machine-written polynucleotides may fluoresce in response to such light. The fluorescence profile of the fluorophores associated with the machine-written polynucleotides may enable reading of the nucleotide sequences of those machine-written polynucleotides. To pick up such fluorescence, the flow cell 800 of the present example further includes a lower integrated circuit layer 890 with a plurality of image sensors 892. By way of example only, the lower integrated circuit layer 890 and image sensors 892 may be part of a CMOS chip.

The lower integrated circuit layer 890 and image sensors 892 are integrated into the lower body portion 806 in this example, with the image sensors 892 being positioned at the lower surface 866 of the lower fluid flow channel 762. In some other variations, the lower integrated circuit layer 890 and image sensors 892 are integrated into some other component. By way of example only, the lower integrated circuit layer 890 and/or image sensors 892 may be integrated into a cartridge (e.g., the removable cartridge 200) that receives the flow cell 800; may be integrated into the base instrument 102; or may be integrated in some other component.

Each image sensor 892 is positioned under a corresponding well 830. Thus, when the microLED panel(s) 844 is/are activated to emit light toward the well(s) 830 during a reading stage, the corresponding image sensor(s) 892 is/are configured to detect fluorescence emitted by fluorophores associated with polynucleotides (e.g., machine-written DNA) contained within the well(s) 830. The fluorescent light profile detected by image sensors 892 may be utilized to read the polynucleotides as described herein.

It should be understood from the foregoing that microLED panels 844 may be utilized both during a writing stage (e.g., when light frequencies cause selective activation/deposition of nucleotides) and during a reading stage (e.g., similar to light source 560 described above in the context of flow cells 500, 601). Alternatively, two separate light sources may be used—one that is only used during a writing stage and another that is used only during a reading stage. As yet another illustrative alternative, the flow cell 800 may be a "write only" flow cell where the image sensors 892 are omitted such that the microLED panels 844 are only used during a writing process.

C. Printhead for Selective Delivery of Nucleotide Bases

Figure 13:
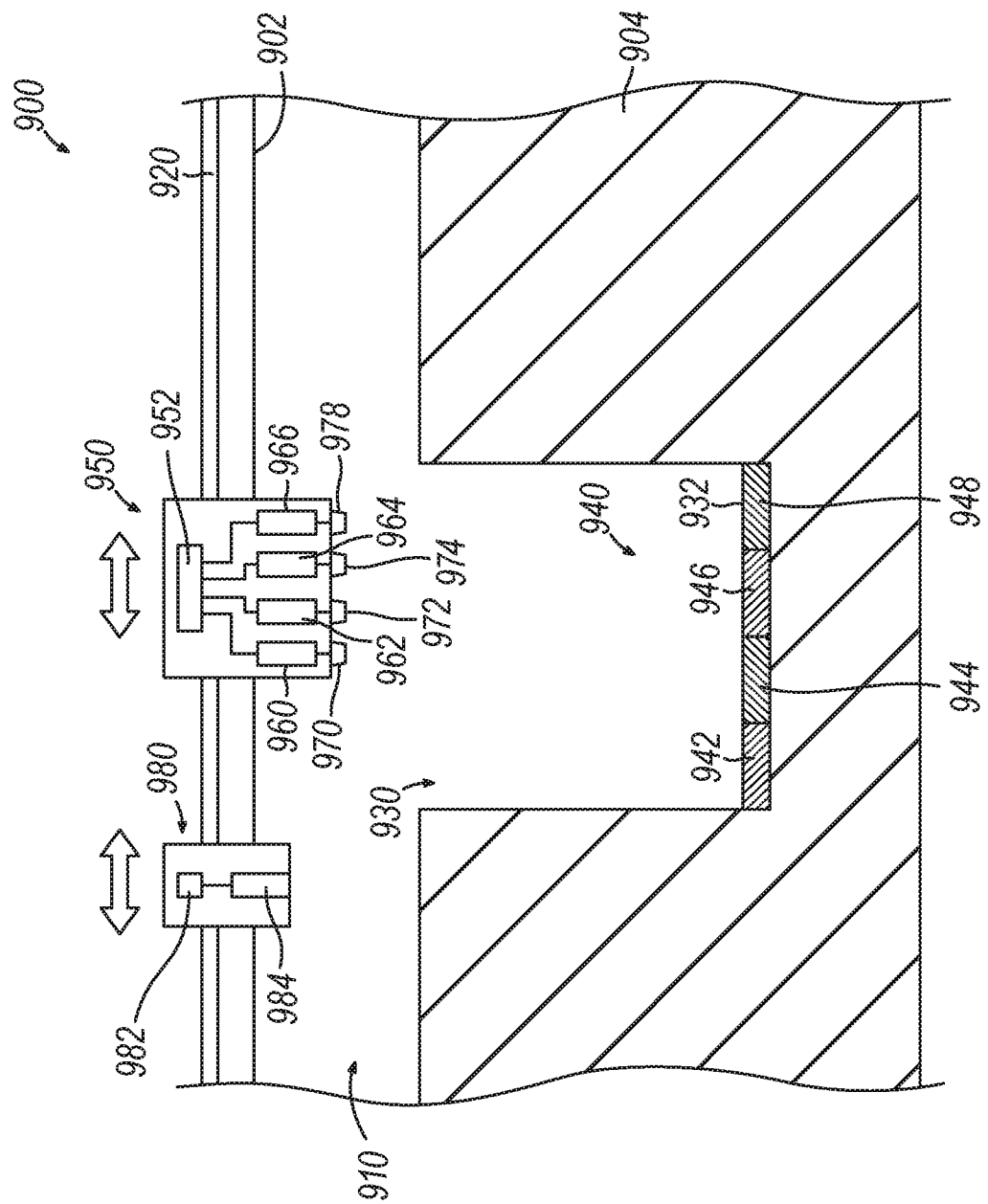
FIG. 13 depicts a block schematic cross-sectional view of another example of a flow cell that may be utilized with the system of FIG. 1.

As another illustrative example, a printhead may be used to selectively deposit nucleotides or nucleobases (e.g., similar to an inkjet printer or additive manufacturing 3D printer, etc.) within a well of a flow cell to thereby machine-write polynucleotides. FIG. 13 shows an example of how this may be carried out. In particular, FIG. 13 shows a flow cell 900 that includes an upper body portion 902 and a lower body portion 904. An upper fluid flow channel 910 is defined between the upper and middle body portions 902, 904. The flow cell 900 of this example lacks a lower fluid flow channel. In some other variations, the flow cell 900 may include a lower fluid flow channel (e.g., similar to the lower fluid flow channel 662 described above).

The flow cell 900 of this example further includes a plurality of wells 930 that are formed as recesses in the bottom surface of the upper fluid flow channel 910. While only one well 930 is shown in FIG. 13, it should be understood that the flow cell 900 may include any suitable number of wells 930 in any suitable arrangement. The bottom 932 of the well 930 includes an electrode assembly 940 that is formed by four electrodes 942, 944, 946, 948. An example of a manner in which the electrode assembly 940 may be operated will be described in greater detail below. It should be understood, however, that electrode assembly 940 may be optional; and that the electrode assembly 940 may be omitted in some variations. It should also be understood that, in variations where the flow cell 900 includes a lower fluid flow channel (e.g., similar to the lower fluid flow channel 662 described above), each well 930 may further include an opening providing a pathway for fluid communication between the well 930 and the lower fluid flow channel (e.g., with or without a valve in such an opening).

In the present example, a guide rail 920 is positioned above the lower body portion 904 of the flow cell 900. A printhead 950 is slidably disposed along the guide rail 920. In some versions, the guide rail 920 and the printhead 950 are integrated into the flow cell 900. In some other versions, the guide rail 920 and the printhead 950 are integrated into a cartridge (e.g., the removable cartridge 200) that receives the flow cell 900. In still other versions, the guide rail 920 and the printhead 950 are integrated into another piece of equipment (e.g., the base instrument 102, etc.). While only one printhead 950 is shown in the present example, other versions of flow cell 900 may have more than one printhead 950 (e.g., an array of printheads 950). Some such versions may have one printhead 950 per well 930. In some such versions, each printhead 950 may remain stationary relative to the wells 930.

The printhead 950 is operable to travel along the guide rail 920 to there by selectively position the printhead 950 over various wells 930 within the flow cell 900. By way of example only, the printhead 950 may include an integrated motor that drives a pinion, with the pinion being engaged with a rack presented by the guide rail 920. Other suitable ways in which the printhead 950 may selectively travel along the guide rail 920 will be apparent to those skilled in the art in view of the teachings herein. It should also be understood that the guide rail 920 may be optional; and that various other kinds of components may be used to provide guided movement of the printhead 950 in relation to the wells 930 of the flow cell 900. Such variations may further enable provide guided movement of the printhead 950 along at last two axes in relation to the wells 930, such that the printhead 950 may be selectively positioned over wells 930 in different rows and columns in the flow cell 900. Again, other suitable ways in which the printhead 950 may selectively travel in relation to the wells 930 will be apparent to those skilled in the art in view of the teachings herein.

The printhead 950 of the present example includes an integral controller 952, a set of nucleobase reservoirs 960, 962, 964, 966, and a set of nozzles 970, 972, 974, 976. The controller 952 may include an integrated circuit and/or any other suitable components as will be apparent to those skilled in the art in view of the teachings herein. Each nozzle 970, 972, 974, 976 is associated with a corresponding one of the nucleobase reservoirs 960, 962, 964, 966. The controller 952 is operable to drive the printhead 950 to expel one particular nucleobase (e.g., adenine) from the nucleobase reservoir 960 out through the nozzle 970; another particular nucleobase (e.g., cytosine) from the nucleobase reservoir 962 out through the nozzle 972; another particular nucleobase (e.g., guanine) from the nucleobase reservoir 964 out through the nozzle 974; and another particular nucleobase (e.g., thymine) from the nucleobase reservoir 966 out through the nozzle 976. Various suitable ways in which this may be accomplished will be apparent to those skilled in the art in view of the teachings herein. By way of example only, the printhead 950 may selectively expel nucleobases through corresponding nozzles 970, 972, 974, 976 using components and techniques similar to those employed in conventional inkjet printers or additive manufacturing 3D printers, etc.

While each nucleobase is expelled through a respective nozzle 970, 972, 974, 976 in this example, other variations may provide a manifold between the nucleobase reservoirs 960, 962, 964, 966 and a single, shared nozzle. All four nucleobases may thus be expelled from the printhead via the same nozzle. In such versions, the printhead may further include a means for purging the manifold and corresponding fluid line to the shared nozzle, with such purging being provided when the printhead is switching over from expelling one nucleobase through the shared nozzle to expelling another nucleobase through the shared nozzle.

It should also be understood that other variations of the printhead 950 may lack the integrated nucleobase reservoirs 960, 962, 964, 966. In some such variations, the nucleobase reservoirs 960, 962, 964, 966 are located elsewhere (e.g., in a cartridge that receives the flow cell 900, in the base instrument 102, etc.). In such variations, flexible fluid lines may couple the nucleobase reservoirs 960, 962, 964, 966 with the corresponding nozzles 970, 972, 974, 976 (or with a manifold that leads to a shared nozzle) of the printhead 950. Such flexible fluid lines may still permit the printhead 950 to move freely relative to the wells 930. Moreover, such flexible fluid lines may still permit the printhead 950 to move freely relative to the nucleobase reservoirs 960, 962, 964, 966 when the nucleobase reservoirs 960, 962, 964, 966 are not integrated into the printhead 950.

It should be understood from the foregoing, that the printhead 950 may be selectively positioned over a particular well 930; then be activated to selectively expel nucleobases from the nozzles 970, 972, 974, 976 in a particular sequence in order to machine-write a polynucleotide. In some versions, the printhead 950 moves in relation to the well 930 between each nucleobase expulsion, in order to successively position each nozzle 970, 972, 974, 976 along the same vertical axis when that nozzle 970, 972, 974, 976 is activated to expel a nucleobase. This may promote deposition of nucleotides in a strand that is aligned with the axis at which each nozzle 970, 972, 974, 976 is activated.

As noted above, each well 930 of the present example further includes an electrode assembly 940 that is formed by four electrodes 942, 944, 946, 948. In this example, each electrode 942, 944, 946, 948 is associated with a particular nucleobase (e.g., similar to the electrode segments 642, 644, 646, 648 described above in the context of FIG. 7). For instance, electrode 942 may be configured to provide a charge that is uniquely associated with adenine; electrode 944 may be configured to provide a charge that is uniquely associated with cytosine; electrode 946 may be configured to provide a charge that is uniquely associated with guanine; and electrode 948 may be configured to provide a charge that is uniquely associated with thymine. Following the above example where certain nucleobases are associated with certain corresponding nozzles 970, 972, 974, 976, the electrode 942 may be activated when adenine is expelled through the nozzle 970; the electrode 944 may be activated when cytosine is expelled through the nozzle 972; the electrode 946 may be activated when guanine is expelled through the nozzle 974; and the electrode 948 may be activated when thymine is expelled through the nozzle 976. Such activation of the electrodes 942, 944, 946, 948 in cooperation with expulsion from the nozzles 970, 972, 974, 976 may further promote formation of machine-written polynucleotides with nucleobases in the desired sequence. In some other versions, the electrode assembly 940 has only one electrode that is operable to activate any nucleobase that is emitted by the printhead 950.

FIG. 13 also shows an acoustic tamping assembly 980 movably positioned on the guide rail 920. The acoustic tamping assembly 980 may have the same kinds of relationships with the guide rail 920 as described above with respect to the printhead 950. The acoustic tamping assembly 980 may also be configured to move in relation to the wells 930 in any of the other manners described above with respect to the printhead 950. The acoustic tamping assembly 980 of this example includes an integral controller 982 and an acoustic transducer 984. The controller 982 may include an integrated circuit and/or any other suitable components as will be apparent to those skilled in the art in view of the teachings herein. The controller 982 is operable to selectively drive the acoustic transducer 984 to emit acoustic waves downwardly toward the well 930. Various suitable forms that the acoustic transducer 984 may take will be apparent to those skilled in the art in view of the teachings herein. It should also be understood that the acoustic tamping assembly 980 may be integrated into the printhead 950, such that it is not necessarily required to provide the acoustic tamping assembly 980 and the printhead 950 as separate components. Moreover, the acoustic tamping assembly 980 may be omitted altogether in some versions.

In operation, the printhead 950 may first be activated deposit one or more nucleobases in a well 930; and the acoustic tamping assembly 980 may then be activated to acoustically tamp the deposited nucleobase(s) in the well 930. For instance, the printhead 950 may be positioned over a particular region of the well 930 to deposit the selected nucleobase(s); then the printhead 950 may be moved out of the way; then the acoustic tamping assembly 980 may be moved into place over that particular region of the well 930 to acoustically tamp the deposited nucleobase. This acoustic tamping may ensure that the nucleobase emitted by the printhead 950 reaches the intended well 930. The acoustic tamping may also prevent diffusion from occurring between the wells 930. In versions where the acoustic tamping assembly 980 is integrated directly into the printhead 950, a sequence of movement of the printhead 950 and then the acoustic tamping assembly 980 may not be necessary.

In addition to the foregoing, any of the flow cells and writing processes described herein may utilize a photoacid (e.g., changing the pH within a well by activating an acid with light). In addition, or in the alternative, any of the flow cells and writing processes described herein may utilize methylation to increase encoding space (e.g., allowing use of methylated adenine, methylated cytosine, methylated guanine, and/or methylated thymine in addition to of adenine, cytosine, guanine, and thymine). In addition, or in the alternative, any of the flow cells and writing processes described herein may utilize selective dehybridization, where an enzyme is hybridized to inhibitor (e.g., providing selective inhibition and/or anchoring an enzyme to a spatially localized region). In addition, or in the alternative, any of the flow cells and writing processes described herein may utilize varying currents to draw polynucleotides to a desired location or release the polynucleotide (e.g., to assist in transferring polynucleotides from one region of space to another region of space; or from one device to another device). In addition, or in the alternative, any of the flow cells and writing processes described herein may utilize pre-charged enzymes to provide selective deposition or activation of particular nucleotides.

VIII. Miscellaneous

All of the references, including patents, patent applications, and articles, are explicitly incorporated by reference herein in their entirety.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

As used herein, an element or step recited in the singular and proceeded with the word "a" or "an" should be understood as not excluding plural of said elements or steps, unless such exclusion is explicitly stated. Furthermore, references to "one implementation" are not intended to be interpreted as excluding the existence of additional implementations that also incorporate the recited features. Moreover, unless explicitly stated to the contrary, implementations "comprising" or "having" an element or a plurality of elements having a particular property may include additional elements whether or not they have that property.

The terms "substantially" and "about" used throughout this Specification are used to describe and account for small fluctuations, such as due to variations in processing. For example, they may refer to less than or equal to ±5%, such as less than or equal to ±2%, such as less than or equal to ±1%, such as less than or equal to ±0.5%, such as less than or equal to ±0.2%, such as less than or equal to ±0.1%, such as less than or equal to ±0.05%.

There may be many other ways to implement the subject technology. Various functions and elements described herein may be partitioned differently from those shown without departing from the scope of the subject technology. Various modifications to these implementations may be readily apparent to those skilled in the art, and generic principles defined herein may be applied to other implementations. Thus, many changes and modifications may be made to the subject technology, by one having ordinary skill in the art, without departing from the scope of the subject technology. For instance, different numbers of a given module or unit may be employed, a different type or types of a given module or unit may be employed, a given module or unit may be added, or a given module or unit may be omitted.

Underlined and/or italicized headings and subheadings are used for convenience only, do not limit the subject technology, and are not referred to in connection with the interpretation of the description of the subject technology. All structural and functional equivalents to the elements of the various implementations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

What is claimed is:

1. A method comprising:
   flowing a fluid through a flow channel of a flow cell, the fluid comprising a plurality of types of nucleotides, the flow cell including a plurality of primary bases to support polynucleotides, the primary bases being secured to a floor region of the flow cell;
   selecting one type of nucleotide for attachment to a selected primary base of the plurality of primary bases in the flow cell; and
   activating the selected one type of nucleotide to thereby cause the selected one type of nucleotide to attach to the selected primary base, the attached nucleotide representing machine-written data, activating the selected type of nucleotide comprising applying a change in pH within the flow cell, the applied pH being associated with the selected type of nucleotide.

2. The method of claim 1, further comprising repeating selecting one type of nucleotide for attachment to a selected primary base in the flow cell and activating the selected one type of nucleotide to thereby cause the selected one type of nucleotide to attach to the selected primary base, to thereby generate a polynucleotide on the primary base, the generated polynucleotide including a plurality of selected types of nucleotides, the generated polynucleotide representing machine-written data.

3. The method of claim 1, activating the selected type of nucleotide comprising activating an electrode in the flow cell to thereby apply a voltage to the selected type of nucleotide.

4. The method of claim 3, each type of nucleotide being associated with a particular voltage, activating the electrode comprising activating the electrode to apply the particular voltage associated with the selected type of nucleotide.

5. The method of claim 4, the flow cell including electrodes associated with different corresponding voltages, the method further comprising selecting an electrode from the electrodes, the selected electrode corresponding to the voltage associated with the selected type of nucleotide, the activated electrode being the selected electrode.

6. The method of any claim 1, activating the selected type of nucleotide comprising communicating pre-charged enzymes to the flow channel.

\* \* \* \* \*